United States Patent
Umeda et al.

(10) Patent No.: US 7,577,555 B2
(45) Date of Patent: Aug. 18, 2009

(54) APPARATUS AND METHOD FOR DETERMINING PATTERNS OF DAMAGE BEING CAUSED IN ROLLING CONTACT ELEMENT

(75) Inventors: Atsushi Umeda, Okazaki (JP); Tsutomu Shiga, Nukata-gun (JP); Kouichi Ihata, Okazaki (JP)

(73) Assignee: Denso Corporation, Kariya (JP)

( * ) Notice: Subject to any disclaimer, the term of this patent is extended or adjusted under 35 U.S.C. 154(b) by 329 days.

(21) Appl. No.: 11/492,775

(22) Filed: Jul. 26, 2006

(65) Prior Publication Data

US 2007/0044543 A1    Mar. 1, 2007

(30) Foreign Application Priority Data

Jul. 26, 2005  (JP)  ............... 2005-215378

(51) Int. Cl.
  G06F 17/10  (2006.01)
(52) U.S. Cl. ........... 703/2; 703/7; 702/34; 702/42; 384/49; 384/50
(58) Field of Classification Search ......... 703/2, 703/6, 7; 702/33–35, 41, 42; 29/724; 267/267; 384/7, 18, 19, 49, 50
  See application file for complete search history.

(56) References Cited

U.S. PATENT DOCUMENTS

2002/0046012 A1    4/2002  Takemura et al.
2006/0064197 A1    3/2006  Shiga et al.

FOREIGN PATENT DOCUMENTS

| EP | 1 184 813 A2 | 3/2002 |
|---|---|---|
| EP | 1 686 500 A2 | 8/2006 |
| JP | B2 06-089783 | 11/1994 |
| JP | A 2005-018916 | 1/2005 |
| JP | A 2005-025437 | 1/2005 |
| JP | A 2006-018088 | 1/2006 |

OTHER PUBLICATIONS

Zaretsky, Erwin V., "A. Palmgren Revisited-A Basis for Bearing Life Prediction," NASA Technical Memorandum 107440, pp. 0-8, XP002404923, May 18-22, 1997.

Ahluwalia et al., "Computer-Aided Optimum Selection of Roller Bearings," *Computer-Aided Design*, vol. 25, No. 8, pp. 493-499, XP000385103, Aug. 1993.

Kato, K, "Classification of Wear Mechanisms/Models," Proceedings of the Institute of Mechanical Engineering,. vol. 216, No. J6, pp. 349-355, XP001247684, 2002.

*Primary Examiner*—Russell Frejd
(74) *Attorney, Agent, or Firm*—Oliff & Berridge, PLC

(57) ABSTRACT

A method of designing a roller bearing is disclosed upon clarifying mechanisms of damage patterns in respect of two kinds of brinelling, involved in the bearing, wherein white-banded flaking (brittle flaking) is a plastic instability phenomenon appearing under high-speed deformation accompanied by adiabatic shear deformation status with the resultant occurrence of adiabatic shear band (also called white band) inside material of the bearing. This enables all of the damage patterns to be determined upon making comparison between shear strain and shear strain rate, occurring inside the bearing, and discriminated values.

14 Claims, 13 Drawing Sheets

INNER RACE

UNFALKED BALL

OUTER RACE

FIG. 6

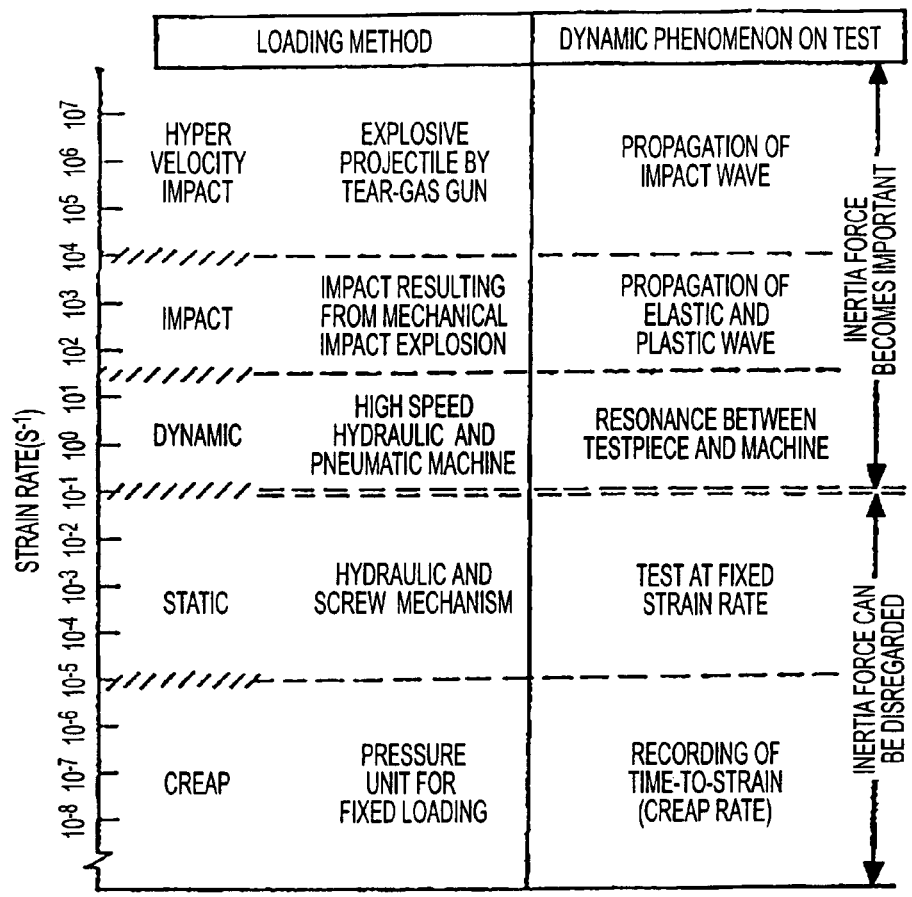

FIG. 7

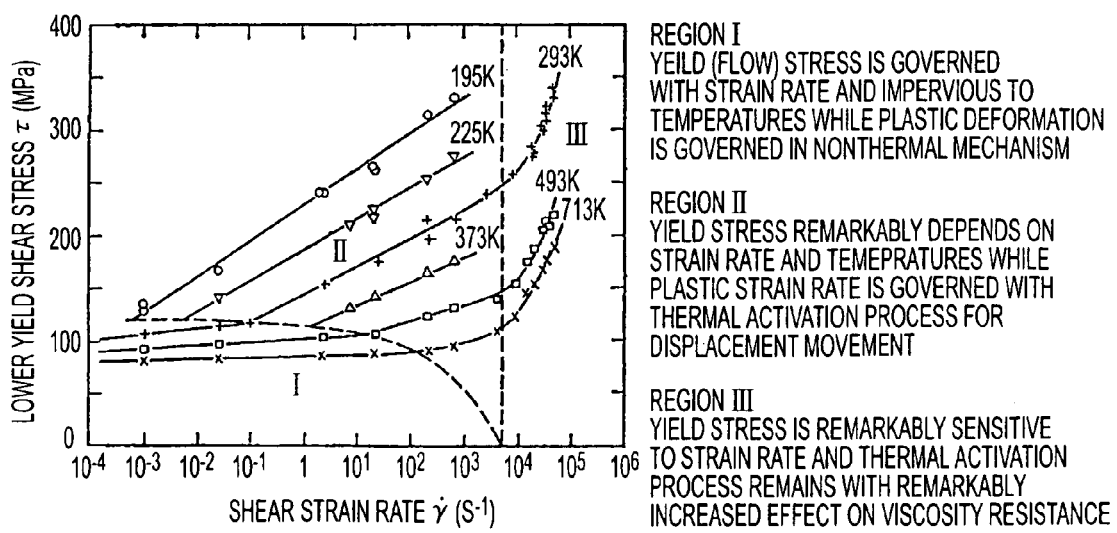

REGION I
YEILD (FLOW) STRESS IS GOVERNED WITH STRAIN RATE AND IMPERVIOUS TO TEMPERATURES WHILE PLASTIC DEFORMATION IS GOVERNED IN NONTHERMAL MECHANISM

REGION II
YIELD STRESS REMARKABLY DEPENDS ON STRAIN RATE AND TEMEPRATURES WHILE PLASTIC STRAIN RATE IS GOVERNED WITH THERMAL ACTIVATION PROCESS FOR DISPLACEMENT MOVEMENT

REGION III
YIELD STRESS IS REMARKABLY SENSITIVE TO STRAIN RATE AND THERMAL ACTIVATION PROCESS REMAINS WITH REMARKABLY INCREASED EFFECT ON VISCOSITY RESISTANCE

PILING-UP

PILING-UP

SINKING-IN

SINKING-IN

PILING-UP

WITH INCREASED STRAIN

WITH DECREASED STRAIN

SINKING-IN

WITH INCREASED STRAIN

WITH DECREASED STRAIN

BARE METASL  WITH INCREASED DEFORMATION

WITH DECREASED DEFORMATION

APPARATUS AND METHOD FOR DETERMINING PATTERNS OF DAMAGE BEING CAUSED IN ROLLING CONTACT ELEMENT

CROSS REFERENCE TO RELATED APPLICATIONS

This application is related to Japanese Patent Application No. 2005-215378 filed on Jul. 26, 2005, the content of which is hereby incorporated by reference.

BACKGROUND OF THE INVENTION

1. Technical Field of the Invention

The present invention relates to an apparatus and method for determining patterns of damage being caused in a rolling contact element such as rolling bearings including a roller baring, and in particular, to a design technique for clarifying the relationship between a damage pattern in a contact area of the rolling contact element and stress to avoid the rolling contact element from abnormal damage.

2. Description of the Related Art

A rolling element, playing a role as a mechanical element, that is, among others, a roller bearing in common use suffers from damages in various patterns. Despite the bearing playing a role as an important component part, there are many probabilities in which no definite solution is obtained to clarify what is to be made to avoid such damages. What can be solely considered in design on a preliminary stage includes only two aspects of obtaining a rolling fatigue life upon calculation of a fundamental dynamic rated load (generally designated by "C") and a way of precluding the occurrence of permanent deformation by calculating the fundamental dynamic rated load. That is, with a consequence of the fatigue life, a final damage pattern results in pitching or flaking. Moreover, when experienced with permanent deformation, the damage pattern results in brinelling (in a brinelling indentation). Despite such brinelling, the bearing suffers from, in addition to such a damage pattern, other damages in various patterns. For instance, these include a pseudo indentation (false brinelling), cracks, chips, fretting, incisura and galling or the like. All of the causes for these phenomena are clarified but no distinct solution is provided for which of a threshold value of the cause results in the occurrence of damage to the bearing. Therefore at the current status quo, it is quite difficult to make a design of a bearing in a preliminary stage to avoid such phenomenon.

In addition to this status quo, recently, roller bearings of various auxiliary-unit component parts such as an alternator of an automotive engine, an air conditioning unit and idler pulley have come to be used in recent years under severe conditions involving vibrations and temperatures or the like. This results in exposure of flaking accompanied by variation in tissue under new patterns. Flaking takes place in any area of the component parts such as an outer race, an inner race and balls (or rollers) and has a feature differing from a fatigue life experienced by a commonly used roller bearing. This is a damage pattern wherein once the fatigue life occurs, flaking occurs on the component part of the bearing within a shortest time period (in the order of approximately $1/100$ to $1/1000$ times that of the related art). A feature of this damage pattern is that is does not exhibit a tissue (in the form of a so-called DEA: Dark Etching Area) which is seen to be upon subject to an etching process with nital liquid as done in a fatigue life test of the related art but to exhibit another tissue (in a white band that is a so-called WEA: White Etching Area).

In a field of bearings, this flaking is called brittle flaking or white-banded flaking with a view to differentiating the same from the fatigue life referred to in the related art. FIG. 1 shows an example of a raceway track of a bearing entered with flaking in a white-band. To be different from a consequence in which all of roller bearings, subjected to rolling life tests conducted on flaking based on a fatigue in the related art practice, are caused to suffer from fatigue breakdown on a final stage, no mechanism of such brittle flaking has been determined yet. Such brittle flaking has a specificity wherein flaking occurs on the bearing within an extremely short time period when experienced breakdown under certain circumstances of recurrence test conditions but no brittle flaking takes place under conditions with no breakdown. Therefore, under a status where a first aid measure is taken with no distinctive scientific basis, no full-scale measure has been taken in this status quo.

A major candidate on a mechanism of such white-banded flaking (brittle flaking) is based on a hydrogen theory. That is, this theory stands on the ground that a ball is caused to slip due to stress such as vibrations applied to the bearing in use and heat and pressure develop in the bearing to cause the decomposition of grease into hydrogen with the resultant occurrence of flaking due to hydrogen brittleness. On the ground of such a theory, various attempts have heretofore been taken to avoid the occurrence of flaking by applying a raceway with an oxide film so as to preclude the separation of hydrogen from grease as disclosed in Japanese Patent Publication No. 6-89783 or to prevent generated hydrogen from entering the raceway. However, as a result of various tests conducted by the present inventors, these attempts have not always been successful in the prevention of flaking. Upon recurrence tests under other conditions than those of the tests conducted on the above attempt with a desired effect, instead, no effect is found and a worse phenomenon is turned out. Certainly, a bearing made of steel forcedly added with hydrogen in a preceding step undergoes white-banded flaking within a short time interval during a test in most of the conditions but no conclusion was obtained in the bearing wherein grease is decomposed into hydrogen during normal operation to cause hydrogen to penetrate into steel resulting in white-banded flaking due to hydrogen brittleness.

Further, another mechanism, a stress theory (a vibration theory in the sense of stress) has been advanced. That is, this theory is a way of thinking to attempt for explaining the occurrence of flaking in terms of stress. This theory falls in the same contradiction as that of the stress theory in that no distinction is possible between flaking based on the stress theory and a commonly experienced fatigue life (accompanied by DEA) based on shear stress. Further, upon various tests conducted on bearings with a real machine (automobile) by the present inventors, flaking has occurred in the bearings and research work has been conducted to find out the relationship between stress and flaking. As a result of such research, the present inventors have determined a fact that during operation of the alternator in a low belt tension, the belt tension is zeroed (to be less than 0 Kg) due to adverse affect of an inertial force caused by engine deceleration and, accordingly, white-banded flaking has appeared only when a drop clearly occurred in load exerted to the bearing at a value of 0 Kg. Such an exemplary case is hard to be explained in terms of the stress theory. Although the other explanation is omitted herein, the stress theory falls in the same contradiction as the hydrogen theory and, therefore, even if countermeasure had been taken on bearings on the ground of the stress theory, white-banded flaking had still occurred in the bearing on a real machine.

As set forth above, none of the mechanisms meets actual conditions for brittle flaking to take place in new types of damage patterns and it is completely unclear to determine which of stress factors of a real machine adversely affects on the occurrence of flaking. Accordingly, a situation stands on the ground with no capability of taking measure on a design of the bearing. In addition, a modern engine adopts a serpentine drive system with a plurality of pulleys driven by a single belt for the purpose of minimizing an engine with lightweight. With such a structure, an issue progressively arises in an increase in belt tension, belt resonance and promoted engine vibration or the like and under such conditions bearings suffer from stress in a complicated pattern. None of the theories, proposed in the past as mentioned above, have made solutions to the occurrence of such brittle flaking. In spite of the roller bearing playing a role as the important mechanical element component part, not only full-fledged measure had not been taken to address the issue of brittle flaking but also even the mechanism for addressing such issue had not been established.

Further, certain damage with mild brinelling has come to be found in a bearing installed on an alternator employing a modern serpentine drive system (see FIG. 2). While this damage looks like false brinelling (also referred to as mild fretting) at the first glance, this damage is not actually associated with an incidence of wear and formalized as brinelling. Among bearings subjected to mild brinelling, some bearings have come out to consequences wherein due to adversely affect resulting from such mild brinelling, balls of the bearings tend to be worn each in a band-like configuration to evolve into a pattern liable to be mistaken to be grinding burn. So to say, as mild brinelling progresses (as a primary failure), the bearing has encountered with damage in a new mode such as band-like wear and pseudo grinding burn or the like as a secondary failure (FIG. 2 shows a photograph of one of a large number of mild brinelling occurring on a raceway track of an inner race of a ball bearing whose ball has encountered with band-like wear).

In the related art practice, although the resulting indentation has been explained as false brinelling resulting from vibration exerted to the ball during a stop of rotation of the alternator, no probability occurs for vibration to be imparted to the bearing because the alternator comes to a halt during a stop of the engine. Although there is a common idea in that the bearing is subjected to vibration accompanied by an indentation during a transportation of an automobile on a ship or a trailer, no way exists for mild wear to take place because damage of this kind has not been recognized in bearings of the related art belt drive system prior to the employment of a serpentine drive system and even during a halt of an engine, belt tension has prevented the bearings from being subjected to undulation resulting from vibrations caused during transportation. Thus, no chance takes place for mild wear to occur (with damage accompanied by a wear phenomenon being defined in the related art to be false brinelling or fretting). Moreover, upon observing the picture of FIG. 2 in detail, although a surface seems to be indented, an indentation has a bottom on which a grinding mark is left and although plastic deformation is present, no wear is present.

Accordingly, the present inventors had made it clear that this mark is a shallow indentation in the form of mild brinelling so to say. If the primary failure (in the form of mild brinelling) can be suppressed, then, no various secondary failures induced from such a primary failure take place and, therefore, a need arises to suppress the occurrence of mild brinelling but even such a mechanism has not been established in the related art.

As set forth above, although the roller bearings take the various damage patterns, what is a guideline to be useful for designing the bearing in advance includes only flaking in a fatigue life and brinelling in permanent deformation and other patterns have had no guideline to be useful for designing the bearing. Further, in spite of an extremely short operating life resulting from brittle flaking caused in a modern bearing as compared to that of a commonly experienced fatigue life (no problems had arisen in alternators in actual practice), no mechanism for explaining such a phenomenon has been established and a situation stands with no capability of taking appropriate measure to address the issue. With no alternatives, woefully inefficient methods in irregular measures have heretofore been taken in this status quo for each of the auxiliary units of the engines upon conducting a test of the bearing on a real machine for confirmation. This results in wasteful efforts involving a step of manufacturing a bearing with an unnecessary increase in size or a bearing with increased prevision. Even with such attempts, such an inconvenience could not be completely addressed. Also, no mechanism for the occurrence of mild brinelling in a modern bearing had been clarified in the status quo. However, the damage patterns include damages in other patterns, resulting from other causes than the mechanical factors (e.g., seizing and electric corrosion), which are scientifically clarified. Thus, description of such damage patterns is herein omitted.

In such a way, although the roller bearings are involved in a variety of mechanical damage patterns, none of the relationships (except for a part thereof being clarified) between a source of cause and stress has been clarified. Attempts have been taken on measures relying on know-how and no measure had addressed all of the issues in advance when designing the bearing.

SUMMARY OF THE INVENTION

The present invention has been completed with a view to addressing the above issues and has an object to provide a method of designing a roller bearing to be of assistance in preventing the bearing from mechanical damage by providing capabilities of clarifying factors of all damage patterns in a primary failure caused in the roller bearing and preventing the roller bearing from damage and enabling judgment of all the damage patterns using a size of one physical quantity (ex stress, load etc.) to make it possible for everybody to make design of the bearing in a simplified fashion with no error.

To address the above issues, the present inventors have come to thinking in that first, the damage patterns can be distinguished from each other to some extent depending on whether deformation exceeds an elastic limit. That is, these damage patterns may be classified into:

a damage pattern, occurring within the elastic limit, which takes the form of flaking or pitching (such as a pit probable to appear in flaking on an initial stage thereof and hereinafter included in flaking with the present invention) caused by fatigue; and a damage pattern, occurring when deformation exceeds the elastic limit, which takes the form of brinelling, cracks, chips, wear, false brinelling and fretting.

Here, it is so clueless about which of the damage patterns corresponds to brittle flaking in the form of new damage. Therefore, research study has been conducted whether to have capabilities in figuring out a mechanism of brittle flaking and subsequently consolidating overall damage patterns in terms of one physical quantity.

Therefore, a recurrence method on brittle flaking has been reconsidered upon returning to the starting line. That is, in the related art practice, recurrence tests on flaking of a bearing (as influenced by usual fatigue life) had been conducted to cause white-banded flaking to reoccur in the bearing upon tests conducted by applying the bearing with large stress such as high loads, high-speed rotations, high temperatures and high vibrations or the like. In contrast, with the present invention, attention has been focused on the incidence of flaking in a bearing installed on a real machine even under a condition (with no load of 0 Kg) with seemingly no feature as set forth above. That is, a consideration has been made that some kind of hints may be obtained upon conducting simulation in faithful accordance with operating conditions of an engine. As a result of such consideration, it has been considered to utilize operating characteristics of the engine, as shown in FIGS. 3A and 3B, which has not been taken into consideration in the related art recurrence tests. That is, this represents a test method incorporating the occurrence of fluctuations in rotation of an internal combustion engine (engine) caused by explosions thereof depending on the number of cylinders.

The recurrence tests have been conducted using an alternator under a method wherein a motor is controllably rotated, with a view to making simulation of a real four-cylinder engine, by causing rippled rotations to occur at an average rotating fluctuation rate of 2% in the order (equivalent to the order of explosions of the engine) of value two times the rotational speed. The motor was rotated at up-and-down speeds and lateral resonance (in a direction of a stretched string) was set to lie in a middle range of the up-and-down speeds. For other conditions, completely ordinary stress was applied to the bearing with no vibration, normal temperatures and no load on the alternator. This condition is very low in stress in contrast to that of an actual engine and represents a condition for the stress theory of the related art because of the absence of occurrence of fixed load, fluctuating loads and vibration. The tentative theories (including both of the hydrogen theory and stress theory) of the related art have tendencies with emphasis on loads with the resultant tendency in which the recurrence tests have conducted upon applying large bearing loads and large vibrations. On the contrary, for the purpose of pretending to clarify a mechanism of the dame patterns, the present test has been conducted on a ball bearing with a reduction in stress that has been placed with emphasis in the recurrence tests of the related art.

As a result, a ball of the ball bearing installed on a front pulley encountered so-called brittle flaking in a white band after a slightly elapsed time of 450 hours (with only one ball among eight balls encountered flaking). That is, white-banded flaking occurred on the ball under a quite common condition that would not be conceived at all in the related art theory. Also, to take a look at the ball bearing, a large number of ellipse indentations with the substantially same size were observed on both of non-flaked balls and an inner race (with the ball having an indentation with a depth deeper than that of the inner race) but no indentation was observed on an outer race (see FIGS. 4A and 4B).

FIG. 5A shows a photograph of a raceway of the inner race. The indentation in the form of a contact ellipse with a major axis of 2.6 mm is observed on the raceway (with the indentation being visible in a crescent-shaped pattern due to influence of a curvature because of the shooting in an oblique direction). FIG. 5B shows a result of the indentation, formed on the ball in the same ellipse shape as that of the inner race, whose depths were measured for positions in a major axis direction (with a spherical surface of the ball being developed on a planar surface for displaying a depth of the indentation). The ellipse had a central area, which had remained intact in a surface condition of the ball with no formation of the indentation, and a peripheral area formed with a indentation in a deep shape. The raceway of the inner race has the same shape as that of the ball in an area except for the indentation shape having a shallow depth.

That is, the ball bearing has encountered clearly mild brinelling as shown in FIGS. 5A and 5B. The indentation clearly remained intact in the ellipse shape, resulting from contact between the ball and the raceway with no wearing powder being visible, which was a mark clearly resulting from one contact. With such incidences, the indentation is not a micromotion-wearing phenomenon like false brinelling (mild fretting) but brinelling resulting from one impact. As a result of a further detailed analysis conducted on these experimental tests, assumption was made that the indentations resulted from the occurrence of strain inside the ball in plastic region and of the indentations, an object with increased plastic deformation encountered a white band accompanied with flaking. (In view of the fact with no indentation formed on the outer race, flaking has occurred due to stress acting on only the ball and the inner race. That is, such a state means an impact phenomenon between the ball and the inner race.)

That is, the present inventors have come to a conclusion that white-banded flaking on the present bearing is a result of a plastic instability phenomenon induced at high speed strain that is referred to in an impact work field and the white band is an "adiabatic shear deformation band" (otherwise known as a "white band"). Before giving a detailed description, two characteristic information handled in such a field are supplemented. First, the stress-strain relationship of material during high-speed deformation takes a value fairly different from that of the relationship obtained in a material test conducted at a low speed in normal practice (wherein the term "high speed" means a region in impact load greater than a the strain rate of $10^2$/sec like a value shown in FIG. 6). For example, FIG. 7 shows the relationships among a the strain rate, temperatures and yield shear stress in terms of an example of soft steel for discussion in an image of regions II and III. Secondly, large strain is handled. For instance, the maximum shear strain (strain at a fracture point) $\gamma_z$ marks an extremely high level in a value ranging from 0.5 to 5 (in a stretch approximately 10 to 100 times that of a static material test).

The "adiabatic shear deformation band" in such an impact field occurs under a mechanism in which as a shear strain rate $\dot{\gamma}$ is extremely high, a localized area falls in an adiabatic condition. If shear strain $\gamma$ is high under such an adiabatic condition, high heat develops in a localized area due to resulting strain energy and, additionally, after the impact (heating) has been finished, the localized area at high temperatures is rapidly quenched with a cold mass around a peripheral area. As a result, the localized area takes a tissue nearly close to a quenched status. This localized tissue, called an "adiabatic shear deformation band", is visible to be white in color with high strength steel and called as a white band. This white band means a white band occurring in a roller bearing.

That is, the "adiabatic shear deformation band" occurs when shear strain $\gamma$ and the shear the strain rate $\dot{\gamma}$ are extremely high and exceed certain limit values ($\gamma_c$, $\dot{\gamma}_c$).

With such a theory, the present inventors have calculated the limit values of a bearing made of commonly used material (SUJ2), with a result expressed in Equation 11 in an average value.

$$\gamma_c = 0.15, \dot{\gamma}_c = 10^4/\text{sec} \tag{Eq. 11}$$

The tests have demonstrated an outcome that when factors such as shear strain and shear the strain rate exceed these limit values, a white band occurs. Further, in order to absolutely avoid the occurrence of the white band in view of irregularity in material SUJ2, it is safe for the bearing if the factors do not exceed values of Equation 12 expressed below.

$$\gamma_c=0.08, \dot{\gamma}_c=10^2/\text{sec} \quad \text{(Eq. 12)}$$

Hereunder, the present invention is described below using the average Equation 11 with a view to allowing an actual phenomenon (a phenomenon occurring in normal practice) and an image to match each other.

Such a strain rate does not belong to load in static or dynamic categories shown in FIG. 6 in nature but to a phenomenon with a category in an impact condition. A physical quantity expressed in such stress belongs to a field that is to be discussed not based on load but on an impact speed (m/sec). It was found that the white band had been commonly known in an impact work field. As a result of using such a theory on the impact field and calculating a condition by which the ball bearing does not exceed the two limit values described above, it is turned out that with a bearing in a commonly used size, if a ball bears an impact speed of a value less than 1 m/sec (under a 'want' condition equivalent to Equation 12), the above factors do not exceed the above limit values with no occurrence of white-banded flaking whereas if the impact speed substantially exceeds a value of 3 to 4 m/sec (thus a 'must' condition should be less than 3 m/sec, which is equivalent to Equation 11) with the occurrence of flaking. It will thus be easily understood that the higher the impact speed, the higher will be strain $\gamma$ and the strain rate $\dot{\gamma}_c$.

It is thus clarified that this impact causes the occurrence of an indentation (brinelling) in an ellipse shape. In a case where the impact speed is high, the bearing encounters brinelling in the form of a deep indentation and, in contrast, if the impact speed is low, the bearing encounters mild brinelling. Further, it is clarified that even if the bearing encounters an impact with the same impact speed, the bearing undergoes mild brinelling under a situation where strain $\gamma$ of an inner race in a concave curvature has a less value than that of the ball with a convex curvature and strain $\gamma$ becomes less in value with no occurrence of friction on an impact surface. (Even in the structures shown in FIGS. 4A and 4B, the ball has the indentation that is deeper than that of the inner race regardless of the ball and the inner race caused to be brought into contact at the same impact speed. That is, this is the reason why the ball is liable to undergo white-banded flaking.) That is, the present inventors have recognized that damage patterns of brittle flaking can be discussed in terms of levels of strain $\gamma$ and a shear strain rate $\dot{\gamma}$.

Moreover, it has been found out that damage (see FIG. 2) with mild brinelling of recent date has turned out to be the same result as that of FIGS. 5A and 5B. That is, if a contact between a ball and a raceway track is instantaneously interrupted due to the presence of a resonance of a V-ribbed belt and the ball and the raceway track are brought into contact again at an impact speed, then, strain $\gamma$ and a strain rate $\dot{\gamma}$ occur. If these factors lie at small values, mild brinelling takes place on the bearing as shown in FIG. 2 and FIGS. 5A and 5B. On the contrary, if the impact speed is high, then, the strain $\gamma$ and the strain rate $\dot{\gamma}$ come to exceed the limit values of Equation 11 causing brittle flaking to take place.

As briefly described above, the damage patterns of the bearing can be judged in terms of the level of shear strain $\gamma$ and a material characteristic. For instance, FIG. 8A shows the material characteristic in shear stress $\tau$-shear strain $\gamma$ plotted in terms of various the strain rates of material including tool steel S-7 (it will be appreciated that the bearing undergoes extremely large strain as set forth above). Also, calculation is made using such characteristics to obtain an adiabatic shear strain limit value $\gamma_{\bar{c}}$ that lies at a value of 0.16. The relationship of such material characteristics is plotted on an image view (in a similarity to elastic complete deformation) of FIG. 8B. In FIG. 8B, an elastic area and a plastic area are distinguished from each other in terms of a yield point true shear strain $\gamma_k$; a brittle (white band) breakdown limit value is indicated by true strain $\gamma_{\bar{c}}$; and complete breakdown is indicated by maximal true shear strain (breakdown-point strain) $\gamma_z$. Making comparison between such a characteristic and shear strain $\gamma$ based on such a characteristic and load (ex. load and impact speed) to make judgment on which of the categories is related to strain results in capability of determining a particular damage pattern. That is, this can be achieved merely by plotting resulting strain $\gamma$ in the characteristic curve shown in FIG. 8B. (Provided that in case of a white band, judgment needs to be executed based on the shear the strain rate $\dot{\gamma}$ and the limit value $\dot{\gamma}_{\bar{c}}$ as previously noted.)

Moreover, although a fatigue life can be calculated in terms of shear stress $\tau o$ (which is calculated in terms of load based on a Palmgren's theory), dividing stress $\tau o$ by a shear elastic coefficient G provides a result of $\gamma$ and, hence, it can be concluded that the fatigue life is also calculated in terms of shear strain. That is, all of the damage patterns of the bearing can be expressed in terms of shear strain (including the strain rate) and discrimination values related to strain.

With one aspect of the present invention, a damage pattern of a contact element can be judged upon making comparison between magnitudes of shear strain and a strain rate, occurring in rolling contact elements, and the discrimination values resulting from a material characteristic of the relevant element and loading methods. This makes it possible for the bearing to be designed in a way to avoid the occurrence of damage to a rolling contact area in advance, enabling appropriate measure to be taken.

With a second aspect of the present invention, the discrimination values include five values related to yield point shear strain, adiabatic shear deformation limit strain, an adiabatic shear deformation limit strain rate, breakdown-point shear strain and an impact occurrence strain rate of the loading method. This enables all of the dame patterns to be judged in terms of only a size of a single physical quantity such as shear strain (inclusive of a the strain rate) and everybody can simply make a design of a bearing with no error.

With a third aspect of the present invention, the damage patterns are classified in five concrete damage patterns involving all of mechanical damage patterns and even if anybody makes design of a bearing, no omission or leakage takes place in study.

With a fourth aspect of the present invention, a damage pattern can be judged upon comparison among five discrimination values including shear strain $\gamma$ and a strain rate $\dot{\gamma}$ and yield point shear strain $\gamma_k$, adiabatic shear deformation limit strain $\gamma_{\bar{c}}$, an adiabatic shear deformation limit strain rate $\dot{\gamma}_{\bar{c}}$, breakdown-point true shear strain $\gamma_z$ and impact occurrence strain rate $\dot{\gamma}_I$, making it possible for a further detailed design to be made in a simple fashion.

With a fifth aspect of the present invention, since a material characteristic of steel material for use in a rolling contact area is represented in a concrete numeric value, everybody can simply make a design of a roller bearing in a way to avoid the roller bearing from being damaged.

With a sixth aspect of the present invention, everybody can simply make a design of a roller bearing so as to avoid damage to the bearing in a reliable fashion with no error.

With a seventh aspect of the present invention, a fatigue life of a damage pattern 1 can be discriminated upon life prediction made based on a Miner's principle or corrected Miner's principle using an S-N diagram for shear strain and material and a Weibull establishment distribution, making it easy for flaking to be studied in a widened range.

With an eighth aspect of the present invention, mere simple work for inputting a dimension, material characteristics and loading conditions to a computer enables everybody to simply make judgment on damage patterns of a roller bearing with no error.

BRIEF DESCRIPTION OF THE DRAWINGS

In the accompanying drawings, in which:

FIG. 6 is a view representing the relationship between a strain speed and a loading method;

FIG. 7 is a view showing the relationship between a shear the strain rate of soft steel and yield shear stress;

DETAILED DESCRIPTION OF THE PREFERRED EMBODIMENTS

An embodiment of the present invention will now be described, together with a further description of the mechanism of brittle flaking.

At first, a further detailed mechanism of brittle flaking is described below.

Figure 1:
FIG. 1 is a photograph showing a raceway track formed with a white band accompanied with flaking.

[1] First, description is made of white-banded flaking (brittle flaking) forming a damage pattern like that shown in FIG. 1.

As set forth above, the present inventors have come to the conclusion that the white band constitutes a so-called "adiabatic shear deformation band".

The adiabatic shear deformation band is observed as a white band in high strength steel. This adiabatic shear deformation band is regarded to be a plastic instability phenomenon that appears under high-velocity deformation. According to Stake's study, this theory stands on the ground that as shear strain and a strain rate inside a bearing exceed material-specific threshold limit values ($\gamma_c$, $\gamma_{\dot{c}}$), a white band occurs with the resultant occurrence of cracking and flaking. These values are expressed as $$\dot{\gamma}_c = 10^2 \sim 10^4 / \text{sec} \qquad (\text{Eq. 13})$$

$$\gamma_c = -\frac{C_v n}{\left(\frac{\partial \tau}{\partial T}\right)_{\gamma, \dot{\gamma}}} \qquad (\text{Eq. 14})$$

where Cv represents volume specific heat, n represents a work hardening coefficient, T represent temperature, and τ represents shearing stress.

The material-specific threshold limit values $\gamma_c$, $\dot{\gamma}$ are referred to as adiabatic deformation critical shear strain and an adiabatic shear deformation critical the strain rate, respectively.

Figure 9:
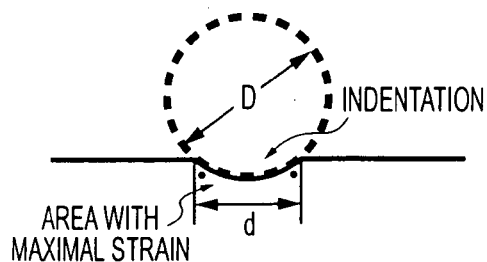
FIG. 9 is a view representing an indentation occurring when a ball is brought into impact with a planar surface.

Substituting these parameters for material (ex SUJ2 etc) of an actual roller bearing results in Equations (11) and (12). With strain γ and the strain rate $\dot{\gamma}$ exceeding values of Equations (13) and (14), a white band is caused to occur (with no occurrence of the white band in the presence of only one factor in excess). Further, the present inventors have come to a conclusion that a phase in which strain and the strain rate exceed the critical values occurs only when a ball (or a rolling element) is brought into collision with a raceway track of an inner race or an outer race and these values are influenced by a collision speed Vo. An indentation (in plastic deformation) occurs on a component part of the bearing at a rate depending on the collision speed Vo and, according to a Taber et al's study, a size of the indentation is correlated with strain γ and the strain rate $\dot{\gamma}$. For example, in the case of an indentation profile shown in FIG. 9, strain has a maximal value, appearing at a peripheral area of the indentation, whose value γ is expressed as $$\gamma \cong 0.3 \frac{d}{D}. \qquad (\text{Eq. 15})$$

Figures 10A, 10B:
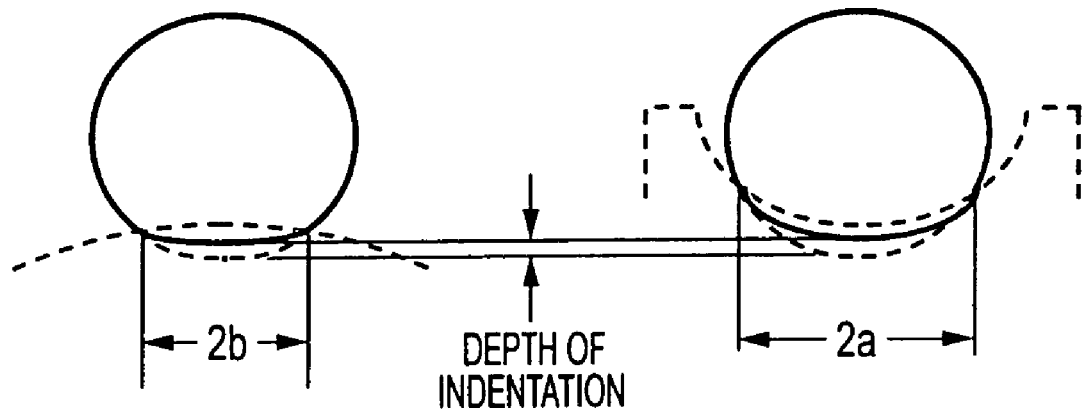
FIGS. 10A to 10C are a front view, a side view and a view of a contact area, respectively, showing shapes of indentations occurring when a ball is brought into impact with a raceway track of an inner race of a ball bearing.
Figure 10C:
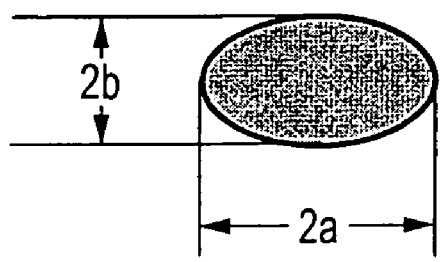

FIGS. 10A to 10C show statuses of contact areas between a ball and a raceway track of an inner race of a ball bearing. FIGS. 10A and 10B are front and side views of the contact areas, respectively, and FIG. 10C shows a contact portion. The indentation resulting from a contact between the ball and the raceway track of the inner race of the ball bearing marks an elliptical shape. With the elliptical shape assumed to have a major axis 2a and a minor axis 2b, a depth of the indentation can be derived in a geometric approach. Suppose an average value (a+b) of the major axis and the minor axis lies in a value of "d", using Equation 15 allows strain γ to be determined. Obtaining strain γ in terms of momentarily varying indentation depths to consider strain in terms of a gradient in relation to a temporal axis allows a the strain rate to be determined.

Figure 3A:
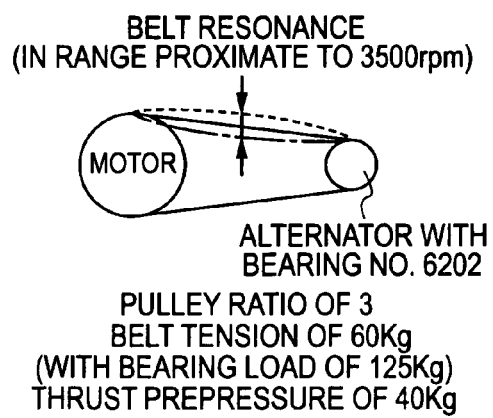
FIG. 3A is a view showing a belt drive system used in a recurrence test conducted by the present inventors for figuring out a mechanism of white-banded flaking (brittle flaking)
Figure 3B:
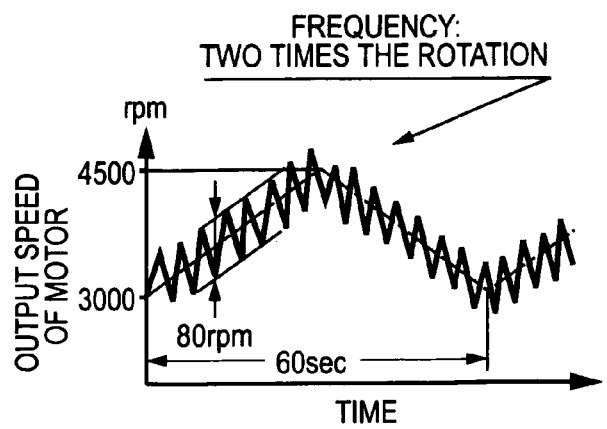
FIG. 3B is a graph showing variation in a rotational speed of a motor plotted in terms of time.
Figure 4A:
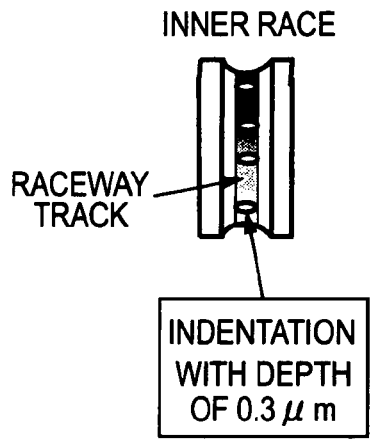
FIGS. 4A to 4C are views showing an inner race having a raceway track formed with an indentation, a ball formed with an indentation with no occurrence of flaking, and an outer race having a raceway track resulting from the recurrence test shown in FIGS. 3A and 3B.
Figure 4B:
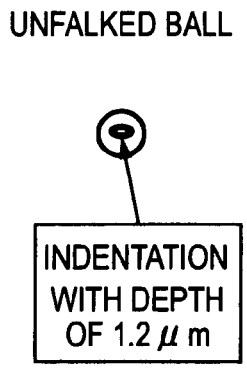
Figure 4C:
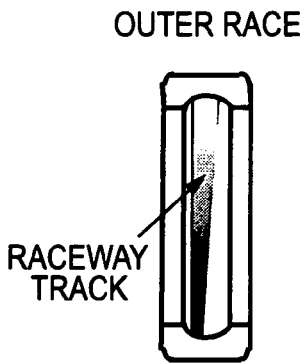
Figure 5A:
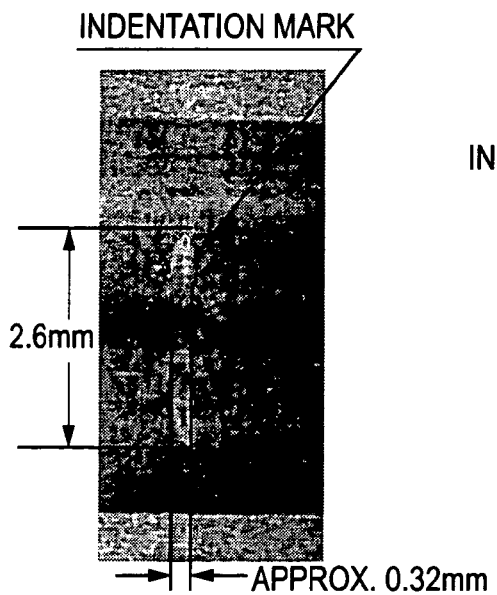
FIG. 5A is an enlarged photograph showing the raceway track of the inner race formed with an indented portion shown in FIG. 4A.
Figure 5B:
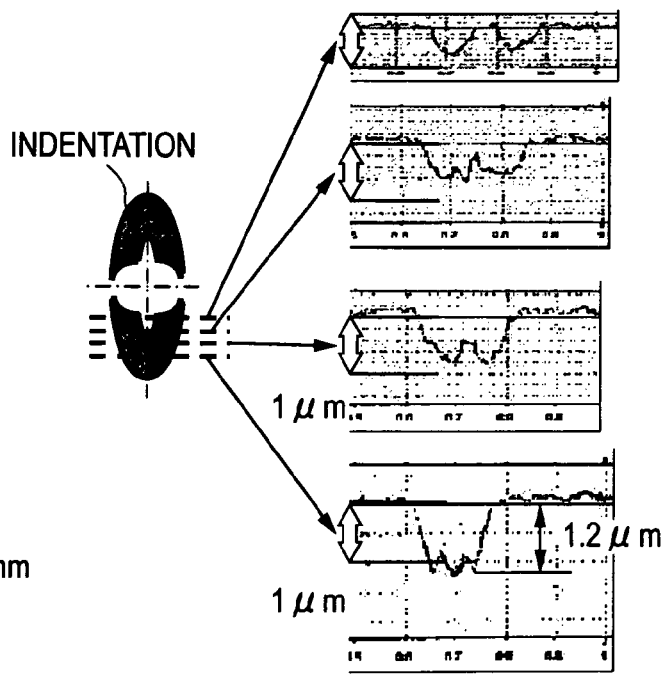
FIG. 5B is a view showing the ball formed with the indentation whose depths are plotted in various levels.
Figure 11A:
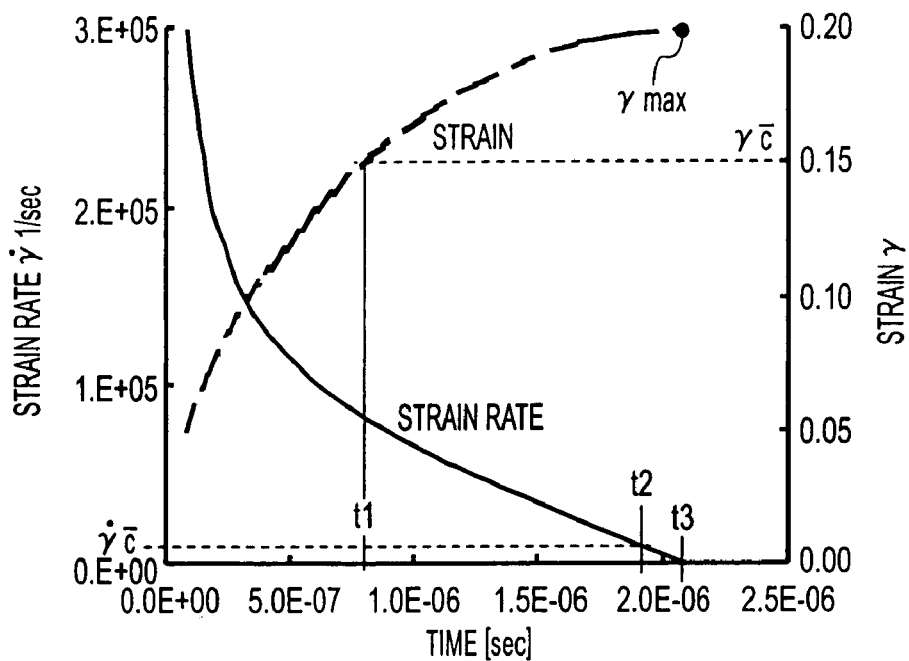
FIGS. 11A and 11B are graphs showing calculation data on dimensions of strain, a the strain rate and an indentation occurring when the ball is brought into impact with the raceway track of the inner race during the recurrence test shown in FIGS. 3A and 3B with FIG. 11A showing variations of strain and the strain rate plotted in terms of time and FIG. 11B showing variation of an indentation in size plotted in terms of time.
Figure 11B:
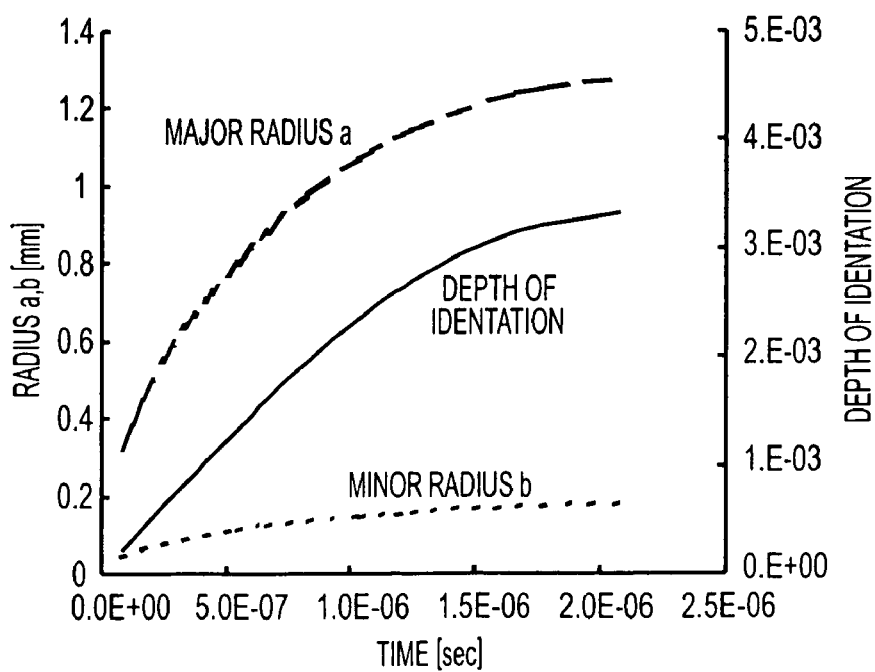

The present inventors have made calculation of these parameters based on such a theory upon incorporating a condition for a recurrence test shown in FIG. 3 and calculation results on these parameters are shown in FIGS. 11A and 11B, respectively. FIG. 11A shows variations in strain and a strain rate of a ball plotted in terms of an elapsed time period (t3 in FIG. 11A) starting from a collision of the ball against a raceway track at a the strain rate of Vo=5 m/sec (representing a value estimated from a shape of an indentation) to a stop of the ball. FIG. 11B shows the relationships between a size of a resulting contact ellipse and a depth of the indentation plotted in terms of time. In FIG. 11A, during a period from time t1 to t2 (0.7E×10$^{-6}$~1.8E×10$^{-6}$ sec), the ball comes to satisfy an adiabatic shear deformation condition (with a critical value expressed by Equation 11) and white-banded flaking is claimed to occur in the ball. In actual practice, the ball had encountered white-banded flaking as described above.

As set forth above, according to the studies conducted by the present inventors, a phase of flaking (hereinafter defined as a damage pattern 4), resulting from an adiabatic shear deformation band (a so-called white band), can be judged depending on whether or not strain γ and the strain rate $\dot{\gamma}$ exceed adiabatic shear deformation critical values $\gamma_c$, $\dot{\gamma}_c$.

Figure 2:
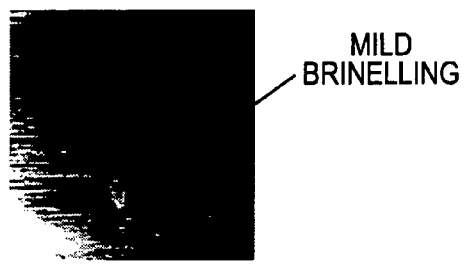
FIG. 2 is a photograph showing mild brinelling.

[2] Next, description is made of a damage pattern with an indentation (dent) formed in a pattern shown in FIG. 2.

Figure 12A:
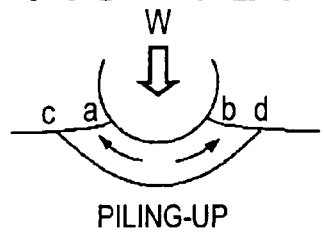
FIGS. 12A and 12B are views showing indentations in "piling-up" shape with FIG. 12A showing a status in which a sphere is pressed against a planar surface and FIG. 12B representing an indentation formed on the planar surface (in permanent deformation)
Figure 12B:
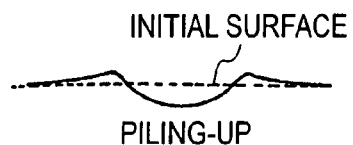

Before entering into a detailed description of the present embodiment, a shape of an indentation handled in a plastic working field is described below. When forcibly pressing a hard sphere against a semi-infinite plane, the semi-infinite plane is formed with indentations with respective shapes in two patterns as shown in FIGS. 12A and 12B and FIGS. 13A and 13B. FIGS. 12A and 12B represent the indentation in one pattern with a peripheral portion formed in a ridge configuration, appearing in material when subjected to work hardening, which is referred to as a "piling-up" formation.

Figure 13A:
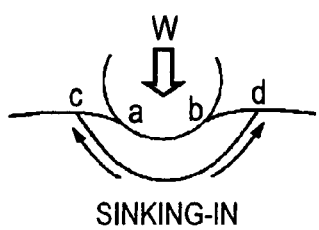
FIGS. 13A and 13B are views showing indentations in "sinking-in" shape with FIG. 13A showing a status in which a sphere is pressed against a planar surface and FIG. 13B representing an indentation formed on the planar surface (in permanent deformation)
Figure 13B:
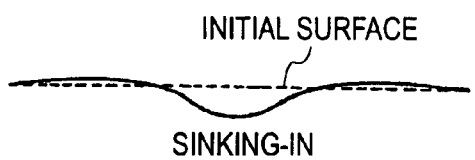

FIGS. 13A and 13B represent the indentation in another pattern with a peripheral portion formed in a sinking configuration, appearing in annealed material when subjected to work hardening, which is referred to as a "sinking-in" formation. FIGS. 12A and 13A are image diagrams showing spheres (balls) prevailing in the middle of pressing movements against planar surfaces with loads W acting in directions indicated by arrows and show flow patterns of materials inside the planes in arrows in FIGS. 12A and 13A. With the "piling-up" formation, the indentation has areas "a", "b" formed in respective ridge portions as shown in FIG. 12A. On the contrary, with the "sinking-in" formation, the indentation has areas "a", "b" formed in respective sinking portions as shown in FIG. 13A.

FIGS. 12B and 13B show the shapes of the indentations left on the planes on final stages with surfaces of the planes on initial stages being indicated by dotted lines in FIGS. 12B and 13B, respectively. That is, the shapes, shown in FIGS. 12B and 13B, represent shapes of the indentations left after curvatures of the indentations are elastically recovered upon unloading loads W, respectively. These shapes represent profiles of the indentations appearing upon elastic recovery that is referred to as a so-called "shallowing effect". (Although it is said that the ridge configuration resulting from the "piling-up" formation has an extent of impact twice the diameter of the indentation, the "sinking-in" formation has a further increased extent of impact and, in actual practice, the indentation is visible in the "sinking-in" formation except for other areas that remain in the mostly same plane intact as the surface on the initial stage.)

That is, the shapes of the indentations are classified into two kinds involving the "piling-up" formation with the occurrence of the ridge portion and the "sinking-in" formation with no occurrence of the ridge portion. In usual practice, a rolling contact component part is made of annealed material for abrasion resistance (while it is a general practice for a bearing to employ quenched and annealed material). Therefore, it has been considered that the shape of the indentation is naturally involved in the "piling-up" formation. Thus, from the standpoint in which no probability takes place for a peripheral area of an indentation to have no ridge portion, a mere indentation with no formation of the ridge portion is considered to be micromotion abrasion. That is, the indentation has been constrainedly determined to be "false brinelling" (also called as minimal fletching). In actual practice, due to the presence of an abrasion mark left in the indentation in the absence abrasion powder as set forth above, such an indentation has been hard to regard to be "false brinelling". Least of all, even an explanation could not be made to clarify a fact that the ellipse had the peripheral area indented with no presence of the indentation in a center area.

Figure 14A:
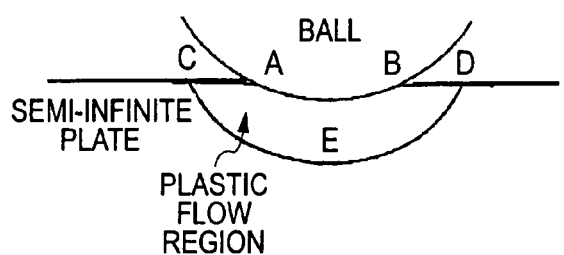
FIG. 14A is a view showing a status wherein a hard ball is pressed against a semi-infinite plate.
Figure 14B:
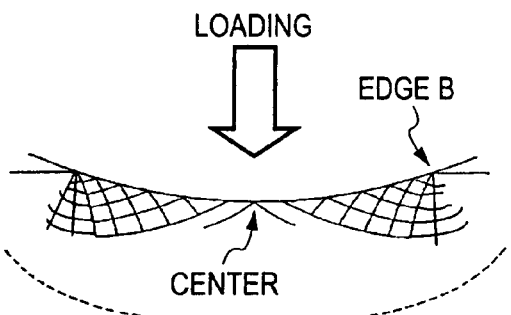
FIG. 14B showing a slip diagram.
Figure 14C:
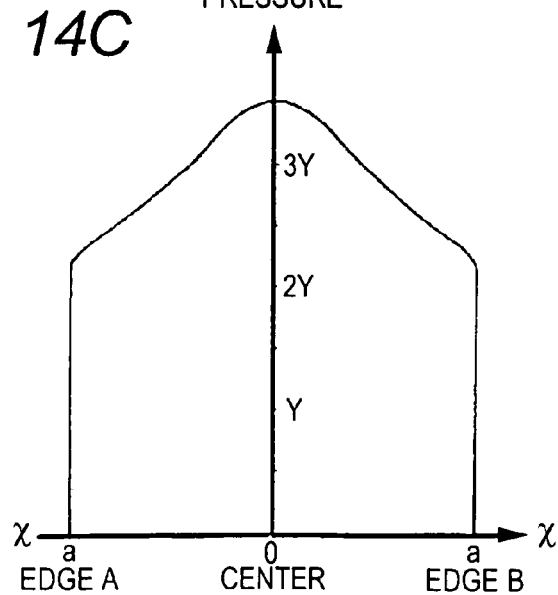
FIG. 14C is a view showing a pressure distribution pattern of a contact surface.
Figure 15:
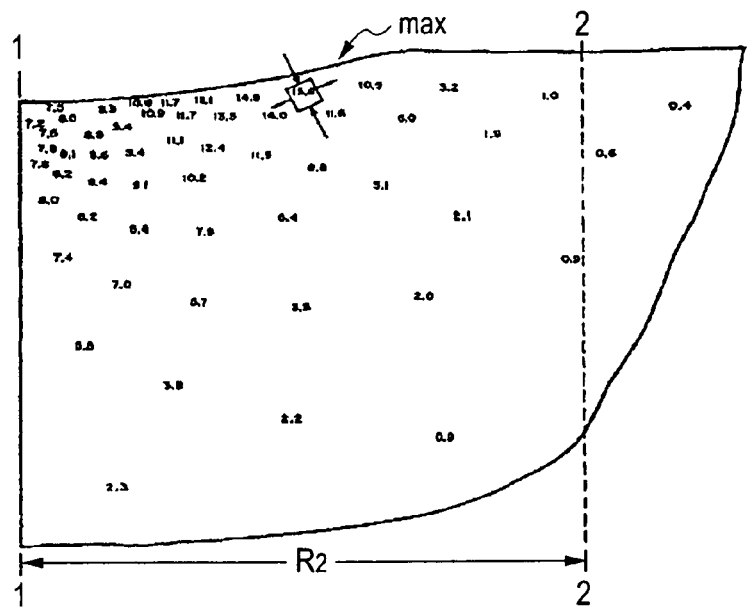
FIG. 15 is a view showing results of calculations for strain of indentationed areas.

The present inventors have attempted to conduct a further research on literatures, playing a role as important information sources of types of damage, which disclose shapes of indentations. FIG. 14A shows a plastic flow region appearing during the formation of an indentation, obtained by Ishlinsky, occurring when causing a hard ball to collide against a semi-infinite plate made of completely plastic material. FIG. 14B shows a slip diagram for the plastic flow region shown in FIG. 14A and FIG. 14C shows a pressure distribution pattern appearing in a contact surface. As shown in FIG. 14C, a center area of the semi-infinite plate suffers from contact pressure with the maximum value of 3.5Y (with "Y" representing yield stress) and, on the contrary, a peripheral portion of the semi-infinite plate undergoes increased stress in concentrated slip lines. FIG. 15 shows calculation results on octahedral plastic strain executed upon computer analysis made by Follansbee et al in actual practice. It is apparent that strain is not maximum at the center area but in the peripheral portion (in contrast to the occurrence of elastic deformation whose center area undergoes high shear stress τSt). This result matches an experimental result demonstrated by Taber. That is, when the semi-infinite plate is subjected to fully plastic deformation, an extent of plastic deformation progresses with higher strain in a peripheral area than that encountered in a center area.

Further, from a standpoint of a shape of an indentation formed under an impact condition of a roller bearing, the roller bearing is usually made of bearing work hardening material and an indentation results in the "piling-up" formation. However, if the roller bearing encounter impact (at an increased the strain rate), then, yield shear stress remarkably increases to a higher extent than that achieved in normal practice as viewed in FIG. 7. That is, it is considered that such a behavior results in apparent processed material (that is, like annealed material).

Therefore, it is assumed that with the bearing subjected to impact, an indentation is formed in the pattern of a "sinking-in" configuration. Moreover, the profiles shown in FIGS. 12A and 13A represent the indentations occurring when the hard spheres are brought into forced contact against the semi-infinite planes under states with the indentations being formed only when one of the sphere and the semi-infinite plane is subjected to deformation. Nevertheless, with the roller bearing, almost no difference exists in hardness among the rolling element (ball), the inner race and the outer race. At such a moment, indentations occur in both the rolling element and the associated component part. That is, it is deemed that the associated component part behaves like annealed material upon subjected to impact in the absence of the difference in hardness among those of the component parts and in view of such a behavior, the indentation is supposed to result in the "sinking-in" formation.

Figure 16A:
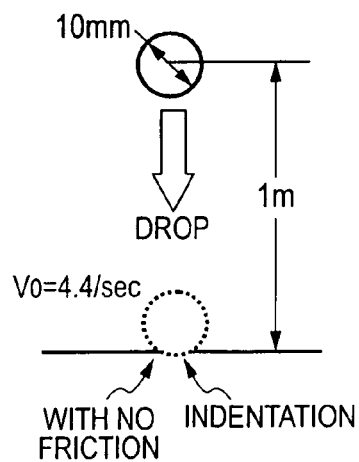
FIG. 16A is a view showing a test method of a ball drop test conducted by the present inventors.
Figure 16B:
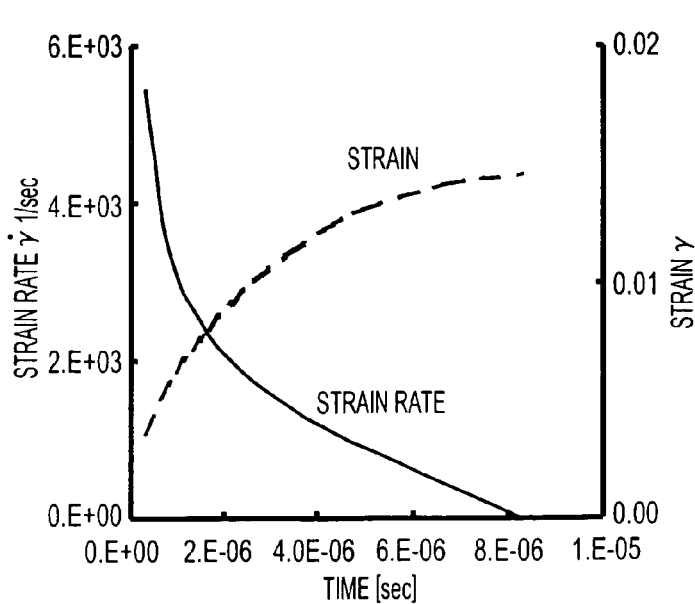
FIG. 16B is a view showing variations in strain and the strain rate occurring in the middle of formation of an indentation.

Therefore, the present inventors have conducted tests using a ball and a flat plate made of ball bearing material such as SUJ2 in order to demonstrate such a phenomenon. That is, a test 1 was conducted using a ball with a diameter of 10 mm that was forcibly pressed against a flat plate (in a test equivalent to a so-called shore hardness test). FIG. 16A shows a condition under which a test 2 is conducted and FIG. 16B shows calculation results on strain and the strain rate (in Equation 15). The strain rate lies in a value in the order of $10^3$/sec that falls in a category of impact load shown in FIG. 6 (with strain belonging to a category in which strain is less and does not satisfy Equation 11 whereby no white band occurs. No white-band occurred in actual practice).

The result was that in the test 1 (with static load), an indentation occurred in the "piling-up" configuration and with the test 2, an indentation occurred in the "sinking-in" configuration. That is, the indentation shape took the "sinking-in" configuration in a phase with impact load.

In consideration of the indentation in light of the above results, two situations are considered. One situation includes a case wherein under a circumstance where the strain rate is high under an adiabatic condition, a quasi-annealed material equivalence is maintained. A second situation includes a case wherein under a circumstance where the strain rate is low under an adiabatic condition, the indentation exhibits that of original process material. Here, suppose a the strain rate (a speed at which an impact is generated) at a boundary with dynamic load and impact load is represented as $\dot{\gamma}_I$ ($\dot{\gamma}_I$=50~$10^2$/sec in the light of the drawing), a shape of the indentation can be organized upon comparison between impact occurrence strain rate $\dot{\gamma}_I$ and the magnitude of the strain rate $\dot{\gamma}$ actually occurring in the bearing. Thus, the shape of the indentation can be organized upon comparison between impact occurrence strain rate and the magnitude of the strain rate actually occurring in the bearing.

(1) In a case where a the strain rate $\dot{\gamma}$ is low (the strain rate<$\dot{\gamma}_I$ . . . static and dynamic load)

Figure 17A:
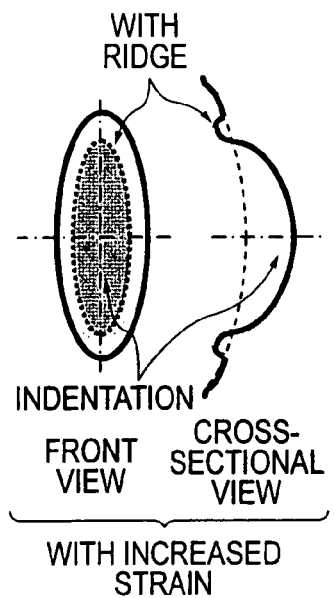
FIGS. 17A and 17B are views showing indentations each formed in a "piling-up" shape in a ball bearing with FIG. 17A showing the indentation formed under increased strain and FIG. 17B showing the indentation formed under lessened strain.
Figure 17B:
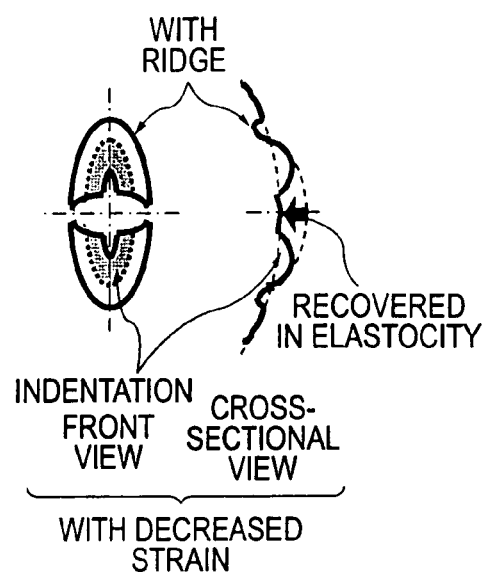

This is a case where a shape of an indentation formed by pressing a ball against a planar surface is left intact. That is, with work hardening material, the indentation results in the "piling-up" formation as shown in FIGS. 12A and 12B and with annealed material, the indentation results in the "sinking-in" formation as shown in FIGS. 13A and 13B. Since the roller bearing is usually made of SUJ2, the indentation results in the "piling-up" formation. The FIGS. 17A and 17B show the indentations resulting in the "piling-up" formation. The indentations have ellipse shapes that have ridge portions resulting from brinelling (brinelling in the so-called "piling-up" formation, which has been referred to in the related art, as shown in FIGS. 17A and 17B. Additionally, a size of the indentation increases in proportion to strain $\gamma$.

With strain $\gamma$ laying at a high value, brinelling takes place in the "piling-up" configuration (see FIG. 17A).

A contact ellipse has a size in proportion to strain $\gamma$.

With strain $\gamma$ lies at a further small value, no elastic deformation is disregarded with respect to plastic deformation and what remains as a permanent set includes a peripheral area with an increase in strain $\gamma$ whereas elastic recovery occurs in a center area when strain $\gamma$ lies at a low level. Moreover, by analogy with Equation 15, strain becomes small in a minor axis than that in a major axis and it is conceived that an overall configuration is observed to include "brinelling" in a "piling-up" configuration in a minor level as shown in FIG. 17B.

Figure 19A:
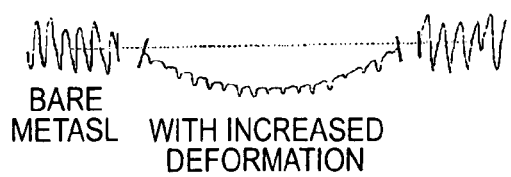
FIGS. 19A and 19B are views showing surface roughness conditions of indentationed portions with FIG. 19A showing the indentationed portion formed in increased deformation and FIG. 19B showing the indentationed portion formed in lessened deformation.
Figure 19B:
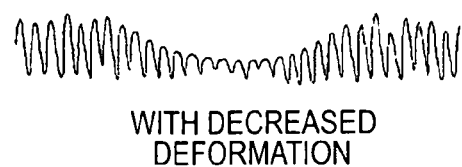

Further, a surface roughness is shown in an image in FIGS. 19A and 19B. FIG. 19A is a view showing a case, representing increased deformation (in an increased strain with high load), wherein an unlevel surface (in surface roughness) of an indentation undergoes plastic deformation with (internal) bare metal and remains in original and individual irregularities (with a roughness remaining in an indented area). FIG. 19B is a view showing a case, representing decreased deformation (in a decreased strain with low load), wherein an unlevel surface (in surface roughness) of an indentation undergoes plastic deformation and a major portion of bare metal is also subjected to elastic deformation.

(2) In case of a high the strain rate $\dot{\gamma}$ (the strain rate>$\dot{\gamma}_I$ ... with impact load)

As described later, the presence of high-velocity deformation results in behavior of annealed material in pseudo-event and it is estimated that such deformation fundamentally results in brinelling in the "sinking-in" configuration.

Figure 18A:
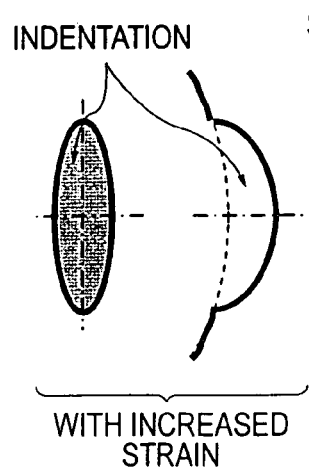
FIGS. 18A and 18B are views showing indentations each formed in a "sinking-in" shape in a ball bearing with FIG. 18A showing the indentation formed under increased strain and FIG. 18B showing the indentation formed under lessened strain.

An increase in strain γ results in brinelling in the normal "sinking-in" configuration (see FIG. 18A). This results in a consequence wherein a size of a contact ellipse is proportional to strain γ.

However, with strain γ remaining in a high value to exceed $\gamma_{\bar{c}}$, an adiabatic shear deformation band (white band) is caused to occur causing flaking with no capability for a trace of an indentation to be normally visible.

Figure 18B:
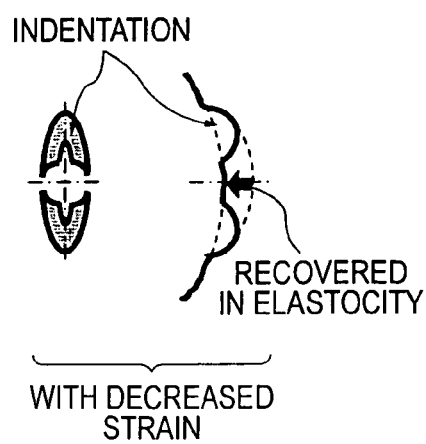

In a case where strain γ lies at a further lower value, no elastic deformation can be disregarded for plastic deformation. It is conceived that the indentation has an overall configuration observed in "brinelling" with a "sinking-in" configuration in a minor level as shown in FIG. 18B.

The indentation has a surface roughness that varies in image in the same manner as those shown in FIGS. 19A and 19B.

The indentations, shown in FIGS. 4A and 4B and FIGS. 5A and 5B and deemed not to actually suffer from the occurrence of white-banded flaking (with a failure to become a white band) but fall in a category (condition) of the impact load mentioned above, were formed in brinelling with the "sinking-in" configuration.

As set forth above, the shapes (shapes of brinelling) of the indentations in the roller bearings are classified into the "sinking-in" configuration and the "piling-up" configuration. It is needless to say that as such phenomena proceed, a secondary failure has a probability of making progress in deteriorated lubrication, seizing, abnormal abrasion, flaking, cracks, etc.

With the above, in speculating the shapes of the indentations, brinelling (hereinafter termed as damage pattern 2), which is conventionally said to appear when applied with high load, is present when the strain rate $\dot{\gamma}$ lies at a small level ($\dot{\gamma}<\dot{\gamma}_I$).

The indentation has a size that varies depending on strain γ.

Further, brinelling (hereinafter termed as damage pattern 3), which has been apt to be confused with false brinelling in the related art practice, is present when the strain rate $\dot{\gamma}$ lies at a high level ($\dot{\gamma}\geq\dot{\gamma}_I$).

In this case, a size of the indentation varies depending on strain γ.

In particular, as strain γ and the strain rate $\dot{\gamma}$ increase beyond $\gamma_{\bar{c}}$, $\dot{\gamma}_{\bar{c}}$ a white band occurs accompanied with flaking (representing the damage pattern 4 described above).

[3] Next, as strain γ further increases beyond a fracture point true strain $\gamma_z$, it is natural that cracks or chips occur (this is termed as a damage pattern 5).

Figure 8A:
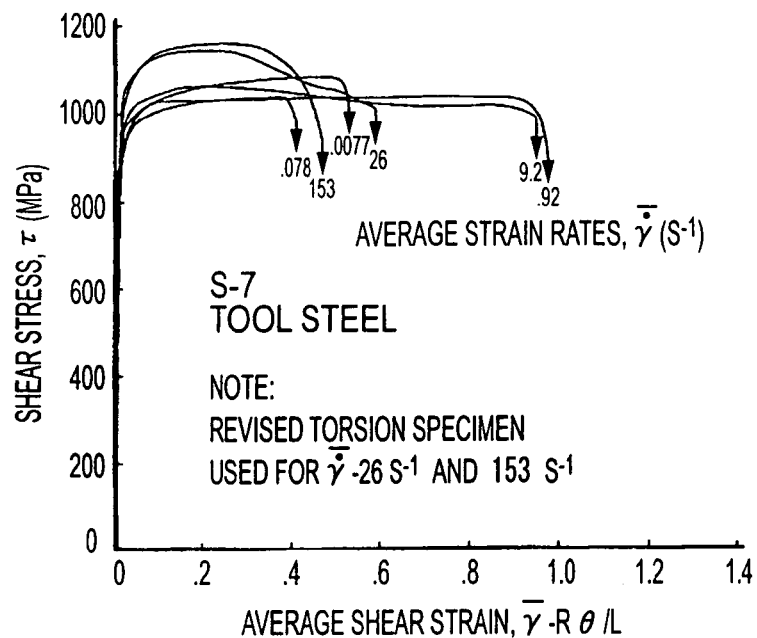
FIG. 8A is a graph showing actually measured values of the relationships between shear stress of tool steel S-7 and shear strain.
Figure 8B:
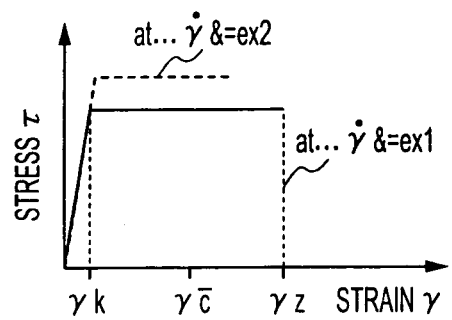
FIG. 8B is a graph showing images of such relationships.

Although the strain rate $\dot{\gamma}$ has no influence on the damage pattern, a value of the fracture point true strain $\gamma_z$ varies depending on the strain rate as shown in FIGS. 8A and 8B.

[4] In contrast, it is needless to say that under a circumstance where strain γ is small and lower than a yield point true strain $\gamma_k$, strain naturally remains within elastic deformation in a damage pattern finally accompanied by flaking or pitching due to fatigue life (this is termed as a damage pattern 1).

Although the strain rate $\dot{\gamma}$ has no influence on the damage pattern, a value of yield point true strain $\gamma_k$ varies in a manner as shown in FIGS. 8A and 8B.

Further, while for the damage pattern 1, the related art practice has employed lifetime calculation based on stress, the present invention contemplates to handle a calculation using strain γ in view of uniformity.

In the related art practice, a fatigue life of a roller bearing has been calculated using a dynamic load rating based on a Palmgraen's theory. Now, an outline of this theory is explained below. That is, with this theory, let's consider dynamic maximal shear stress τo acting on a plane parallel to a surface in an area in depth of zo under a contact surface. Moreover, with a view of a reduction in durability of material with an increase in a volume subjected to stress, assumption is made that cracks occur in material at a micro area with less strength close proximity to the depth zo and spreads to the surface thereby causing flaking to occur. A probability S, in which material of a volume V, encountering stress with repetition rate of N times, can withstand flaking, is given by a Weibull' theory as expressed $$\log. 1/S = f(\tau_0, N, z_0) V \qquad \text{(Eq. 20)}.$$

Here, $$f(\tau_0, N, z_0) \propto \tau_0^c N^e z_0^{-h} \; V \propto a z_0 l \qquad \text{(Eq. 21)}$$

where "c, e and h" represent index numbers; "a" represents a contact ellipse major and minor axes; and "l" represents a length in a circumferential direction of a contact surface.

Substituting load F and dimension for stresses τo and zo in this Equation 20 upon using a Hertz's elastic contact theory gives Equation 22 (with a detail of a function being omitted) as $$\log. 1/S = g(N, F, \text{dimensions}) \qquad \text{(Eq. 22)}.$$

Further, defining load to be "C" when $N=10^6$ and substituting this function in Equation 22 gives $$\log. 1/S = g(10^6, C, \text{in dimension}) \qquad \text{(Eq. 23)}.$$

Now, dividing Equation 22 by Equation 23 results in consequence of extraneous proportional constants being erased. The unerased remaining index numbers "c, e, h" are obtained upon concretely conducting fatigue life tests in technique (so-called experimental values). Thus, an operating life of the bearing is obtained on a final stage. For instance, in case of the bearing, the operating life is derived in a formula expressed as $$N = 10^6 \left(\frac{C}{F}\right)^3. \qquad \text{(Eq. 24)}$$

The above Equation represents the Palmgren's theory that has been still widely used in the world by those skilled in the art for deriving the operating life of the roller bearing. That is, this theory involves a theory based on elastic shear stress τo. However, such a theory has a phase that does not meet the reality and, hence, various studies have been conducted making various partial corrections in part. After all, such attempts could not leave the Palmgren's theory. Further, dynamic maximal shear stress τo, which has been a maximal stronghold of such a theory, is meaningless in fact. Actually, identical results are obtained when applied with stress on any part (in any position and any direction). That is, when finally dividing Equation 22 by Equation 23, factors related to a difference in a position and direction appear as the same factors in denominator and numerator in Equation and disappear. Also, this lastly results in a mere experimental equation.

Thus, the Palmgren's theory in the related art practice handles complicated factors but the most important aspect of this theory has no meaning in a result. Some opinions exist in saying that the Palmgren's theory meets experimental results in actual practice but it is natural because such a theory represents the experimental equation. Above all, this theory is inconvenient in that an operating life is obtained utilizing a Miner's principle based on an S-N diagram in general practice. A mechanical and metallurgical learning system around the theory for the above purpose has been completed with no capability of using learning outcomes in a field of a bearing.

Therefore, the present inventors have executed calculations on an operating life of a bearing with no ground of the Palmgren's theory but using the S-N diagram in general use. That is, a normal method is employed utilizing stress τ and the S-N diagram of material. This result (in an experimental value) completely matches a result of an operating life derived from the Palmgren's theory. That is, the calculation on the operating life can be performed in a theoretically meaningful method without using the Palmgren's theory that is theoretically meaningless. Also, this has an excellent effect in which normal learning outcomes can be momentarily reflected. With the present invention, the damage patterns seem to be judged based on shear strain γ in a unified approach as described above and, hence, study is conducted for fatigue life calculation to be substituted to γ. That is, stress τ results in γ in an elastic range by dividing stress τ by a shear elastic coefficient G.

Calculation based on Miner Principle on Rolling Life

Figure 20A:
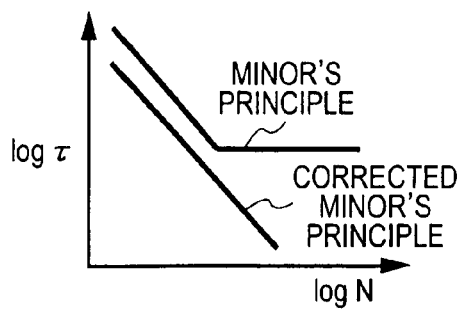
FIGS. 20A and 20B are graphs showing fatigue limit diagrams (S-N diagrams) of material with FIG. 20A showing images and FIG. 20B showing variations in fatigue limits.
Figure 20B:
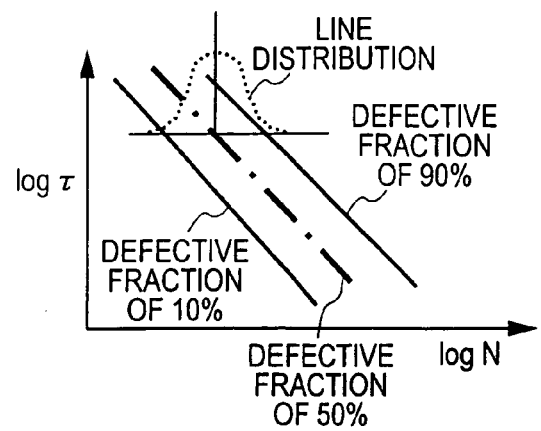

Although FIG. 20A shows a fatigue diagram (S-N diagram) of material, the operating life is calculated based on a corrected Miner principle this time. (In general practice, since the rolling life is said to have no fatigue limit as will be understood from the Palmgren's theory, the calculation is executed on such supposition. Although a concept in which a minimal life is present in a bearing has been proposed in part, in such a case, the calculation is made using the Miner's principle with a consequence described below.) Moreover, the rolling fatigue has a wide stress range to be studied as shown in FIG. 20B. With a view to enables the S-N to be proximate to a straight line, both the longitudinal axis and the horizontal axis are plotted in logarithmic scale. Accordingly, the S-N diagram for the rolling life of bearing material is expressed as $$\log. N = -9 \log. \tau + K \qquad \text{(Eq. 25)}$$

or $$N = K' \tau^{-9} \qquad \text{(Eq. 25')}.$$

Here, "9" represents an inclination in FIG. 20B and is said to appear in case of a fatigue in shear stress (On the contrary, a consequence of "9" being obtained from material tests demonstrates a proof in that the rolling life is subject to shear stress. In case of vertical stress, this index number exceeds a value of 10.) "K" represents a difference in material and takes a value of about 25 in fraction defective of 10% (with a reliability of 90%) of latest bearing material whose fatigue life is improved. (Naturally, $K' = 10^K$)

For instance, according to the Hertz' theory, $$\tau \propto \sqrt[3]{\text{load}}.$$

Substituting this formula to Equation 25' gives $$N \propto \frac{K'}{\text{load}^3}. \qquad \text{(Eq. 26)}$$

Figure 21:
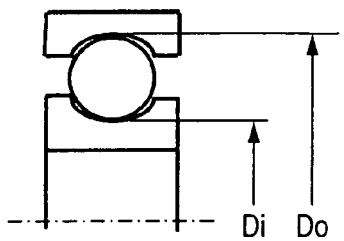
FIG. 21 is a cross-sectional view of a ball bearing.
Figure 22:
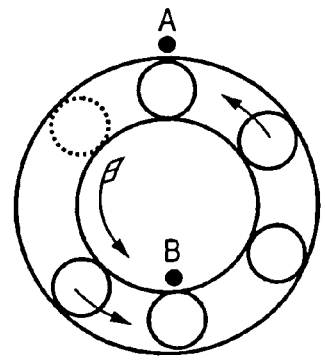
FIG. 22 is a view showing how balls are rolling in the ball bearing.

That is, this results in the same consequence as the result of Equation 24 (defining load, representing a life of $10^6$, to be "C" allows K' to be derived in the same consequence as that of Equation 24). However, the life calculation can be performed based on the S-N diagram with no supposition of rated load C. As an example, when taking a ball bearing with an outer race kept stationary and an inner race rendered rotatable into consideration (see FIG. 21), a revolution of a ball (a rotation of a retainer) per one rotation of the inner race is expressed as $$\frac{D_i}{D_i + D_o}.$$

Therefore, a difference in revolution between the inner race and the ball per one rotation of the inner race is expressed as $$1 - \frac{D_i}{D_i + D_o} = \frac{D_o}{D_i + D_o}.$$

Now, as the balls orbit and are brought into contact with a point A fixed on the outer race in sequence and suppose that the number of balls is Z, the point A is brought into contact with the balls with the number of pieces expressed as $$\frac{ZD_i}{D_i + D_o}$$

(where the number of balls is multiplied by the revolution of the ball).

Likewise, a point B fixed on the inner race is brought into contact with the balls with the number of pieces per one rotation of the inner race as expressed as $$\frac{ZD_o}{D_i + D_o}.$$

Accordingly, as the inner race rotates N-times, the point A is brought into contact with the ball the number of times expressed as $$\frac{ZD_i}{D_i + D_o} N. \qquad \text{(Eq. 27)}$$

The point B is brought into contact with the ball the number of times as expressed as $$\frac{ZD_o}{D_i + D_o} N. \qquad \text{(Eq. 28)}$$

Consequently, in rewriting the fatigue diagram (Equation 25) of material for the inner race and the outer race to enable this diagram to be used for a ball bearing (with Equations 27 or 28 being substituted in place of N in Equation 25), a formula for the outer race (a contact area between the outer race and the ball) can be expressed in one of Equations 29 and 29' expressed as $$\log \cdot N_o = -9 \log \cdot \tau + K - \log \frac{ZD_i}{(D_i + D_o)}. \qquad \text{(Eq. 29)}$$

Or,

-continued $$N_o = K' \frac{(D_i + D_o)}{ZD_i} \tau^{-9} \quad \text{(Eq. 29')}$$

A formula for the inner race (a contact area between the inner race and the ball) can be expressed in one of Equations 30 and 30' as expressed as $$\log \cdot N_i = -9\log \cdot \tau + K - \log \frac{ZD_o}{(D_i + D_o)} \quad \text{(Eq. 30)}$$

$$N_i = K' \frac{(D_i + D_o)}{ZD_o} \tau^{-9}. \quad \text{(Eq. 30')}$$

However, for the purpose of identifying Equations for the inner race and the outer race, suffixes "i" and "o" are attached to "N".

Equations 29, 30 (or Equations 29', 30') represent calculation methods based on the Miner's principle using the ball bearing with the outer race fixed stationary.

Figure 23:
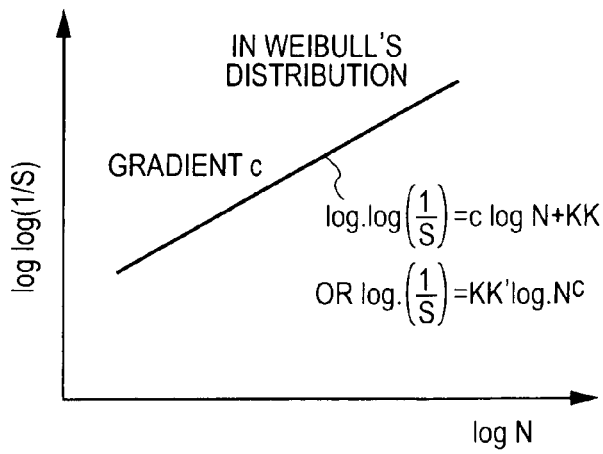
FIG. 23 is a view showing the relationship between reliability in Weibull's distribution and a life.

That is, the calculation method is not started out from the meaningless and indefinite supposition like that made in the Palmgren's theory and can be executed using a normal theory. The calculation may suffice to be executed by incorporating shear stress at the maximum value of repetition amplitude to a portion of $\tau$ (e.g., dynamic and maximum shear stress $\tau$o). It is needless to say that if average stress is present, it is natural for the fatigue diagram (Equation 25) to vary by that extent. Equations 29, 30 (or Equation 29', 30') represent the operating life of the bearing with a fraction defective of 10% in a single attempt with a contact area on either the inner race or the outer race. Therefore, a fatigue life $N_{Assy}$ of a ball bearing "Assy" with a fraction defective of 10% in both of the defectives is derived. Suppose the life has a distribution that follows through the Weibull's theory, formulae are obtained in a manner as understood from FIG. 23 (however, "S" representing a reliability and a value of "0.9" representing a reliability with 90%) and given as $$\log \cdot \left(\frac{1}{0.9}\right) = KK_i' N_i^c \quad \text{(Eq. 31)}$$

$$\log \cdot \left(\frac{1}{0.9}\right) = KK_o' N_o^c. \quad \text{(Eq. 32)}$$

Therefore, for the bearing "Assy", Equation is given as $$\log \cdot \left(\frac{1}{0.9}\right) = (KK_i' + KK_o') N_{Assy}^c \quad \text{(Eq. 33)}$$

In erasing KK'i, KK'o from Equations 31, 32, 33, Equation is given as $$\frac{1}{N_{Assy}^c} = \frac{1}{N_i^c} + \frac{1}{N_o^c}. \quad \text{(Eq. 34)}$$

If shear stress $\tau$ is cleared, a fatigue life of the bearing "Assy" can be calculated based on Equations 29, 30 and 34.

Figure 24:
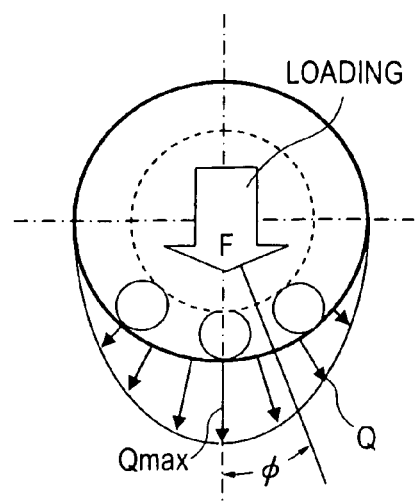
FIG. 24 is a view showing a load distribution pattern of the ball bearing.

However, in actual practice, further processing needs to be executed for obtaining shear strain $\gamma$ based on load F applied to the ball bearing. That is, the bearing has no uniform load distribution pattern over an entire circumference and, so, such a circumstance needs to be considered. With a view to simplifying the calculation, consideration is made that the entire circumference of the bearing remains in uniformly distributed load. However, such substitution is made on consideration to avoid a change in an occurrence probability of fatigue life. Load Q applied to the bearing, shown in FIG. 24, at an arbitrary point thereof is expressed as $$Q = Q_{max}(\cos \phi)^{1.5} \quad \text{(Eq. 35)}.$$

An equivalent rolling element load $\overline{Q}$ (load for the life to be equalized in equivalence) resulting when substituting distributed load in Equation 35 by uniformly distributed load over the entire circumference ($2\pi$ radian) is expressed in terms of the relationship between life and load (see Equation 26) as for an inner race (rolling wheel) (with the same occurrence probability appearing over the entire circumference in nature), $$2\pi \overline{Q}_i^3 = \int_0^{2\pi} Q^3 d\phi$$

where $\overline{Q}$ has a suffix "i" for the inner race.

Substituting the above equation by Equation 35 for rearrangement $$\overline{Q}_i = \left\{\frac{1}{2\pi}\int_0^{2\pi} Q^3 d\phi\right\}^{\frac{1}{3}} = \left\{\frac{1}{2\pi}\int_0^{2\pi} [Q_{max}(\cos\phi)^{1.5}]^3 d\phi\right\}^{\frac{1}{3}}$$

Therefore, Equation is given as $$\overline{Q}_i = 0.5625 Q_{max} \quad \text{(Eq. 36)}$$

for an outer race (stationary wheel) in which different load is present depending on the circumferential position, life establishment is different and needs to be converted to equivalent defective establishment. Substituting Equation 32 by Equation 26 yields $$\log \cdot \left(\frac{1}{0.9}\right) \propto \frac{1}{load^{3c}}.$$

That is, load needs to be converted to equivalent rolling element load on consideration of load influenced with 3c-power for obtaining equivalent establishment. Therefore, $$2\pi \overline{Q}^{3c} = \int_0^{2\pi} Q^{3c} d\phi$$

Substituting the above Equation by Equation 35 for rearrangement gives $$\overline{Q}_o = \left\{\frac{1}{2\pi}\int_0^{2\pi} Q^{3c} d\phi\right\}^{\frac{1}{3}} \quad \text{(Eq. 37)}$$

$$= \left\{\frac{1}{2\pi}\int_0^{2\pi} [Q_{max}(\cos\phi)^{1.5}]^{3c} d\phi\right\}^{\frac{1}{3C}}.$$

-continued

Therefore, $$\overline{Q}_o = 0.5875 Q_{max}$$

where a Weibull's gradient treated as c=10/9 (an experimental value in case of a ball bearing). Here, the relationship between ball load $Q_{max}$ and bearing load F is given by $$Q_{max} = 4.37 \frac{F}{Z}. \quad \text{(Eq. 38)}$$

With the above, a method of calculating a fatigue life using a corrected Miner's principle based on an S-N diagram of material instead of using the fatigue life calculation process based on the Palmgren's theory is briefed below.

With bearing load F being given, load $Q_{max}$ on the ball is given by Equation 34. Using this load on the ball allows equivalent rolling element load $\overline{Q}$ of a contact area between the inner and outer races to be given based on Equations 36, 37. Using the Hertz's elastic contact theory based on equivalent rolling element loads $\overline{Q}_i$, $\overline{Q}_0$ allows respective shear stresses τ to be calculated and fatigue life of the ball bearing "Assy" can be calculated based on Equations 29, 30. The present inventors have conducted the calculation using this method to provide an operating life of the bearing, which has been confirmed to fall in coincidence with the bearing life calculated based on load capacity C.

Although it follows that the rolling fatigue life can be clearly calculated in terms of shear stress τ, the operating life of the bearing can be calculated on a basis of shear strain γ. That is, suppose that the shear elastic coefficient is G, the relationship is given based on Equations 29', 30' as $$N_0 = K' \frac{(D_1 + D_0)}{ZD_1} (G\gamma)^{-9} \quad \text{(Eq. 39)}$$

$$N_1 = K' \frac{(D_1 + D_0)}{ZD_0} (G\gamma)^{-9} \quad \text{(Eq. 40)}$$

$$\frac{1}{N_{Assy}^c} = \frac{1}{N_1^c} + \frac{1}{N_0^c}. \quad \text{(Eq. 41)}$$

Thus, the damage pattern 1 can be possibly indicated in terms of shear strain γ with no recourse on load and stress.

With the above, the present inventors have clarified that all of the mechanical damages of the rolling contact element (e.g., bearing) can be organized and judged in terms of only shear strain and the strain rate. With such clarification, the damage patterns of the rolling contact element can be simply organized in terms of strain and the strain rate.

That is, the damage patterns can be classified into five categories as summarized below.

The pattern 1 represents flaking (inclusive of pitching) resulting from rolling fatigue.

The pattern 2 represents brinelling in the "piling-up" configuration accompanied with induced damage (e.g., a striking mark).

The pattern 3 represents brinelling in the "sinking-in" configuration accompanied with induced damage (e.g., band-like wear).

The pattern 4 represents flaking resulting from an adiabatic shear deformation band (so-called white band).

The pattern 5 represents cracks or chips. These five damage patterns can be determined in terms of the magnitudes of shear strain γ and the strain rate $\dot{\gamma}$.

That is, the relationships are expressed in Equations 42 to 46 as $$\gamma < \gamma_k \quad \text{(Eq. 42)}$$

$$\gamma_k \leq \gamma < \gamma_z \text{ and } \dot{\gamma} < \dot{\gamma}_I \quad \text{(Eq. 43)}$$

$$\gamma_k \leq \gamma < \gamma_z \text{ and } \dot{\gamma}_I \leq \dot{\gamma} \quad \text{(Eq. 44)}$$

$$\gamma_{\overline{c}} \leq \gamma < \gamma_z \text{ and } \dot{\gamma}_{\overline{c}} \leq \dot{\gamma} \quad \text{(Eq. 45)}$$

$$\gamma_z < \gamma \quad \text{(Eq. 46).}$$

With respect to these relationships, the damage patterns 1 to 5 can be established when satisfying the above relationships 42 to 46, respectively. However, shear strain γ (inclusive of the strain rate $\dot{\gamma}$), used in judgment, are taken into consideration on the ground that the shear strain remains in a plastic region and a high strain condition. Thus, it is needless to say that strain γ is not nominal strain but true strain.

Figure 25:
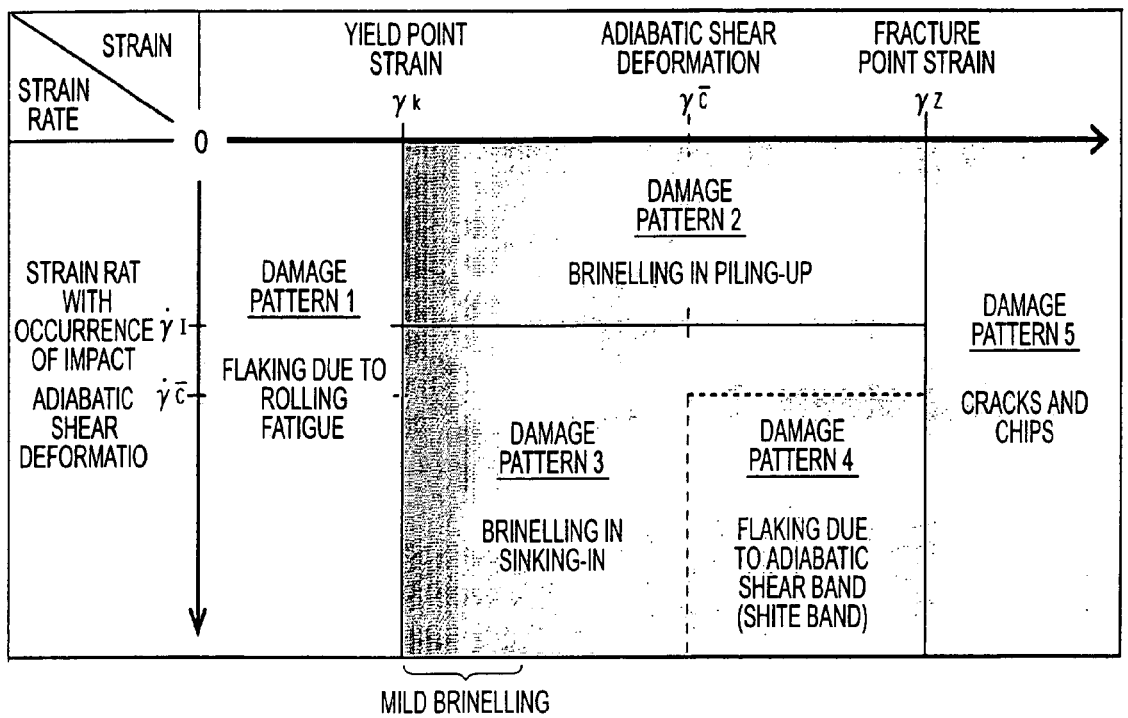
FIG. 25 is a view showing the relationship among strain, the strain rate and damage patterns employed in a method of the present invention.

FIG. 25 shows a table representing the relationships among strain and the strain rates and the damage patterns derived by the method of the present invention. As shown in FIG. 25, the pattern 4 takes the form of the damage pattern involved in the pattern 3. In case of a ball bearing, here, the damage patterns 2 and 3 represent the indentations equivalent to those shown in FIGS. 17A and 18A, respectively. Of these, in particular, in a case where strain γ is closer to $\gamma_k$, the dame patterns take the form of indentation shapes equivalent to those shown in FIGS. 17B and 18B in mild brinelling.

Further, there are materials in which $\gamma_{\overline{c}}$ and $\gamma_z$ have values both of which are substantially coincidence to each other or γ $\overline{c}$ is smaller than $\gamma_z$ in value (in a case where $\gamma_{\overline{c}}$ is greater than $\gamma_z$ in value, it follows that no damage pattern is actually present). Likewise, there is a case where $\gamma_{\overline{c}}$ coincides with $\gamma_I$.

Further, rolling contact element material (e.g., SUJ2) in common use has values indicated below.

$$\gamma_k = 0.002 \sim 0.01 \quad \text{(Eq. 47)}$$

$$\gamma_{\overline{c}} = 0.1 \sim 0.18 \quad \text{(Eq. 48)}$$

$$\gamma_z = 0.02 \sim 1.5 \quad \text{(Eq. 49)}$$

$$\dot{\gamma}_{\overline{c}} \approx 10^4 / \text{sec} \quad \text{(Eq. 50)}$$

($\gamma_k$ and $\gamma_z$ take values including a high strain condition covering static load and impact load and, hence, have values in a wider range than that of strain in a normal case. Further, values of $\gamma_{\overline{c}}$, representing limit values for adiabatic shear deformation to take place, are displayed in average values. Although the limit values in the worst case covering variations correspond to those of Equation 12, the average values fit to a realistic damage pattern more properly in order to make judgment on the damage pattern in common use and, therefore, are adopted.)

Further, an impact occurrence strain rate is expressed as $$\dot{\gamma}_I = 50 \sim 10^2 / \text{sec} \quad \text{(Eq. 51).}$$

That is, judgment values, resulting from material characteristics and methods in which loads are applied, may take the values represented in Equations 47 to 51 and it is conceived that even if these judgment values are used in making judgment of the damage pattern of the actual rolling contact element, the damage pattern can be substantially estimated with no contradiction in an adequate fashion.

Thus, the present invention has turned out the mechanism for flaking to take place due to the white band which has heretofore been unclear to those skilled in the art and clarified that the damage pattern, wrongly referred to as false brinelling in the related art practice, is truly mild brinelling, upon which design study can be made possible to be performed on a preceding stage.

In addition, the related art practice has failed in reorganizing various mechanical damage patterns up to now in respect of all the relationships among causes of flaking and stress (in load). In contrast to such inconvenience, the present invention has clarified concept in which all of the damage patterns can be rearranged on the ground of only the magnitude of one physical quantity of strain (also inclusive of the strain rate because the strain rate represents a change of strain in time and substantially equal to strain). That is, making comparison between a value of strain (including the strain rate) and a discriminated value (based on material characteristic and a load application method) enables a particular damage pattern to be correctly determined in a simplified fashion. This results in capability for distinct measure to be taken and no need arises for taking a quite inefficient method for tests to be conducted on real machines for confirmation as required in the related art practice. Judgment for experimental results can be made in the light of the mechanism with no occurrence of erroneous consequence. Also, no need arises for unnecessarily increasing a size of a bearing or increasing a precision.

Further, judgment of the damage patterns has heretofore been relied on veteran's know-how. Moreover, not only such actual judgment is necessarily correct but also wrong measures have been taken sometime or a size of the bearing has been unnecessarily increased. The designing method of the present invention can be executed on a computer, thereby making it possible for every engineer to simply make design on a roller bearing so as to avoid the occurrence of damages. Thus, the present invention has an excellent advantageous effect in which using a table calculation program in software such as "Excel" in a personal computer enables judgment to be performed through simple operations from input to output operations within one minute.

Figure 26:
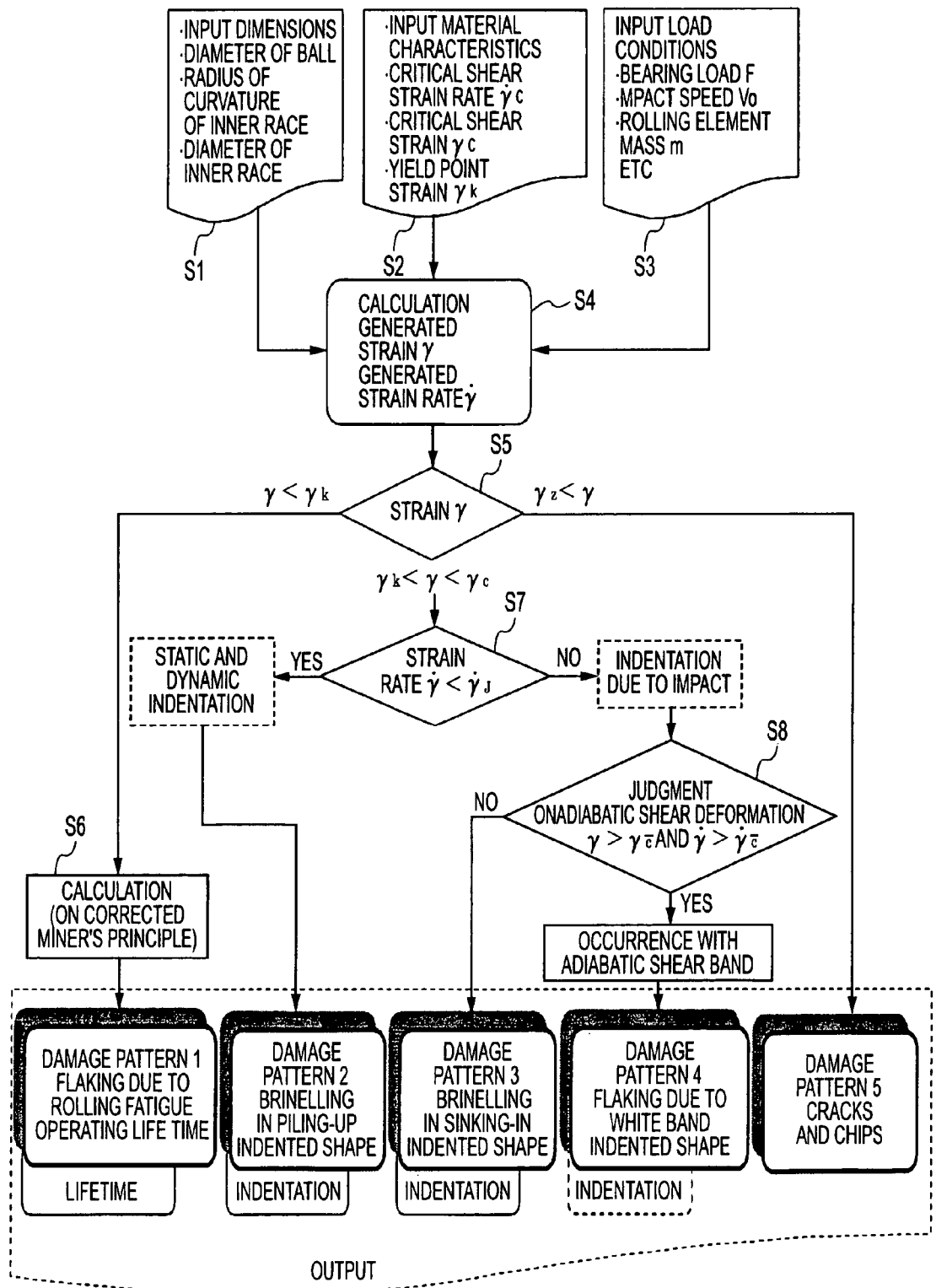
FIG. 26 is a brief of a flowchart for carrying out the method of the present invention for designing a roller bearing using a computer.

FIG. 26 shows a flowchart for making judgment on damage patterns encountered by an actual ball bearing. It is of course needless to explain that the method of the present invention may have not only application to the ball bearing but also application to a design of a commonly used roller bearing.

Figure 27:
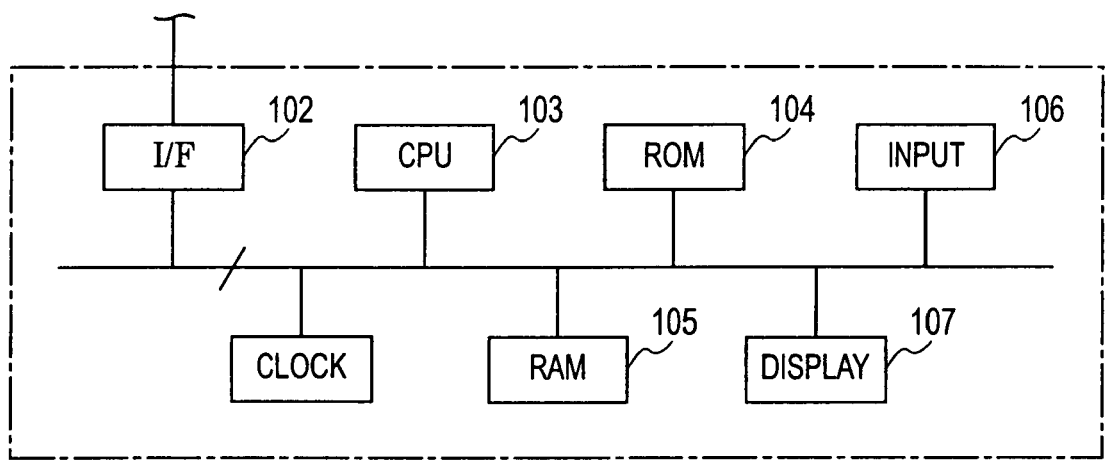
FIG. 27 is a block diagram of a computer which can be used as a determining apparatus according to an embodiment of the present invention.

For example, the processing on the flowchart shown in FIG. 26 can be carried out by a personal computer (or computer) 101 shown in FIG. 27. The computer 101 is provided with an interface 102, CPU (central processing unit) 103, ROM (read-only memory) 104, RAM (random access memory) 105, input device 106, and display 107. Of these the CPU 103 executes a program exemplified in FIG. 26 and data of the program is installed in the ROM 104 in advance. The program shown in FIG. 26 is written to accomplish the judgment of the damage patterns based on the concept according to the present invention.

Specifically, interactively with an engineer, the CPU 103 operates to input dimensions (a ball diameter, a radius of curvature of an inner race, a diameter of the inner race, etc.) at step S1, input material characteristics (a critical shear strain rate $\dot{\gamma}_c$, a critical shear strain $\gamma_c$, a yield point strain $\gamma_k$, etc.) at step S2, and input load conditions (a bearing load F, an impact speed $v_o$, and a rolling element mass m, etc) at step S3. Then, at step S4, the CPU 103 uses those inputted values to calculate both a strain $\gamma$ being estimated and a strain rate $\dot{\gamma}$ being estimated. Further, at step S5, it is determined by the CPU 103 that $\gamma<\gamma_k$, $\gamma_k<\gamma<\gamma_z$, or $\gamma_z<\gamma$.

If the condition Of $\gamma<\gamma_k$ is established at step S5, calculation (on corrected miner's principle) is carried out at step S6 to judge the flaking due to rolling fatigue, so that damage on the damage pattern 1 is judged. If the condition of $\gamma_k<\gamma<\gamma_z$ is established at step S5, it is further determined at step S7 whether or not $\dot{\gamma}<\dot{\gamma}_1$ is met. If this determination is YES, the CPU 103 judges that damage based on the damage pattern 2 has occurred. In contrast, the determination is NO at step S7, it is determined at step S8 whether or not $\gamma>\gamma_c$ and $\dot{\gamma}>\dot{\gamma}_c$. If this condition is not met (NO at step S8), it is judged that damage based on the damage pattern 4 has occurred. By contrast, if the condition is met at step S8 (YES), the CPU determines that the occurrence with adiabatic shear band has occurred to have the damage pattern 4. On the other hand, If the condition of $\gamma_z<\gamma$ is established at step S5, it is judged that damage on the damage pattern 5 has occurred. Information indicating those classified patterns is then outputted from the micro computer.

Moreover, the determining technique according to the present invention will not be confined to the roller baring, but can widely be applied to mechanical element parts having rolling contacts. In other words, any parts can enjoy the merits of the design according to the present invention, as long as there is a potential for occurrence of damage resultant from adiabatic shear bands due to adiabatic shear deformations in cases where stress is applied to such rolling contacts between a rolling member and a stationary member or between two rolling members. Such a contact (parts) is therefore included in transmissions (such as continuously variable transmission (CVT)) and a contact on a tooth plane of a gearwheel as well as rolling bearings. Of course, the rolling bearing includes a ball bearing, a roller bearing, and a needle bearing.

The present invention may be embodied in other specific forms without departing from the spirit or essential characteristics thereof. The foregoing embodiments and modifications are therefore to be considered in all respects as illustrative and not restrictive, the scope of the present invention being indicated by the appended claims rather than by the foregoing description and all changes which come within the meaning and range of equivalency of the claims are therefore intended to be embraced therein.

What is claimed is:

1. A computer-implemented method of determining damage of a mechanical element composed of rolling elements and a stationary member or a component part composed of more than two rolling elements for establishing a rolling contact, the method comprising steps of:
   representing factors of the mechanical element with magnitudes of a shear strain and a shear strain rate occurring in the contact element resulting from an external or internal stress;
   providing discrimination values obtained from material characteristics of the rolling element and a loading method;
   comparing the magnitudes of the shear strain and the shear strain rate to the discrimination values so as to judge mechanical damage patterns of the mechanical element; and
   outputting, as information indicating the damage of the mechanical element, information indicating the judged damage patterns using the computer, wherein
   the discrimination values include five values related to a yield point shear strain, an adiabatic shear deformation limit strain, an adiabatic shear deformation limit strain rate, a breakdown-point shear strain, and an impact occurrence strain rate of the loading method for making judgment on the mechanical damage patterns of the mechanical element.

2. The computer-implemented method according to claim 1, wherein
the mechanical damage patterns are categorized as:
a pattern 1 representing a flaking caused by a rolling fatigue life;
a pattern 2 representing a brinelling in a sinking-up configuration followed by a damage;
a pattern 3 representing a brinelling in a sinking-in configuration followed by a damage;
a pattern 4 representing a flaking caused by an adiabatic shear deformation band; and
a pattern 5 representing a crack or a chip.

3. The computer-implemented method of designing the rolling contact element according to claim 1, wherein
the mechanical damage patterns fall in:
the pattern 1 when Equation 1 is satisfied
the pattern 2 when Equation 2 is satisfied
the pattern 3 when Equation 3 is satisfied
the pattern 4 when Equation 4 is satisfied
the pattern 5 when Equation 5 is satisfied $$\gamma < \gamma_k \quad \text{(Eq. 1)}$$

$$\gamma_k \leq \gamma < \gamma_z \text{ and } \dot{\gamma} < \dot{\gamma}_I \quad \text{(Eq. 2)}$$

$$\gamma_k \leq \gamma < \gamma_z \text{ and } \dot{\gamma}_I \leq \dot{\gamma} \quad \text{(Eq. 3)}$$

$$\gamma_{\bar{c}} \leq \gamma < \gamma_z \text{ and } \dot{\gamma}_{\bar{c}} \leq \dot{\gamma} \quad \text{(Eq. 4)}$$

$$\gamma_z < \gamma \quad \text{(Eq. 5)}$$

where:
$\gamma$ is the shear strain,
$\dot{\gamma}$ is the shear strain rate,
$\gamma_k$ is the yield point shear strain,
$\gamma_{\bar{c}}$ is the adiabatic shear deformation limit strain,
$\dot{\gamma}_{\bar{c}}$ is the adiabatic shear deformation limit strain rate,
$\gamma_z$ is the breakdown-point true shear strain, and
$\dot{\gamma}_I$ is the impact occurrence strain rate.

4. The computer-implemented method according to claim 3, wherein:
the yield point shear strain $\gamma_k$ lies in a value ranging from 0.002 to 0.01;
the adiabatic shear deformation limit strain $\gamma_{\bar{c}}$ lies in a value ranging from 0.1 to 0.18;
the adiabatic shear deformation limit strain rate $\dot{\gamma}_{\bar{c}}$ lies in a value of $10^4$/sec;
the breakdown-point true shear strain $\gamma_z$ lies in a value ranging from 0.02 to 1.5; and
the impact occurrence strain rate $\dot{\gamma}_I$ lies in a value ranging from 50 to $10^2$/sec.

5. A computer-implemented method of determining damage of a ball bearing composed of rolling elements and a stationary member or a component part composed of more than two rolling elements for establishing a rolling contact, the method comprising steps of:
representing factors of a mechanical element with magnitudes of a shear strain and a shear strain rate occurring in the ball bearing resulting from an external or internal stress;
providing discrimination values obtained from material characteristics of the ball bearing and a loading method;
comparing the magnitudes of the shear strain and the shear strain rate to the discrimination values so as to judge mechanical damage patterns of the ball bearing; and
outputting, as information indicating the damage of the mechanical element, information indicating the judged damage patterns from a microcomputer using a display
wherein
the discrimination values include five values related to a yield point shear strain, a adiabatic shear deformation limit strain, an adiabatic shear deformation limit strain rate, a breakdown-point shear strain, and an impact occurrence strain rate of the loading method for making judgment on the mechanical damage patterns of the ball bearing.

6. The computer-implemented method according to claim 5, wherein
the mechanical damage patterns are categorized as:
a pattern 1 representing a flaking caused by a rolling fatigue life;
a pattern 2 representing a brinelling in a sinking-up configuration followed by a damage;
a pattern 3 representing a brinelling in a sinking-in configuration followed by a damage;
a pattern 4 representing a flaking caused by an adiabatic shear deformation band; and
a pattern 5 representing a crack or a chip.

7. The computer-implemented method according to claim 5, wherein:
the mechanical damage patterns fall in:
the pattern 1 when Equation 6 is satisfied
the pattern 2 when Equation 7 is satisfied
the pattern 3 when Equation 8 is satisfied
the pattern 4 when Equation 9 is satisfied
the pattern 5 when Equation 0 is satisfied $$\gamma < \gamma_k \quad \text{(Eq. 6)}$$

$$\gamma_k \leq \gamma < \gamma_z \text{ and } \dot{\gamma} < \dot{\gamma}_I \quad \text{(Eq. 7)}$$

$$\gamma_k \leq \gamma < \gamma_z \text{ and } \dot{\gamma}_I \leq \dot{\gamma} \quad \text{(Eq. 8)}$$

$$\gamma_{\bar{c}} \leq \gamma < \gamma_z \text{ and } \dot{\gamma}_{\bar{c}} \leq \dot{\gamma} \quad \text{(Eq. 9)}$$

$$\gamma_z < \gamma \quad \text{(Eq. 10)}$$

where:
$\gamma$ is the shear strain,
$\dot{\gamma}$ is the shear strain rate,
$\gamma_k$ is the yield point shear strain,
$\gamma_{\bar{c}}$ is the adiabatic shear deformation limit strain,
$\dot{\gamma}_{\bar{c}}$ is the adiabatic shear deformation limit strain rate,
$\gamma_z$ is the breakdown-point true shear strain, and
$\dot{\gamma}_I$ is the impact occurrence strain rate.

8. The computer-implemented method of designing the ball bearing according to claim 7, wherein
the yield point shear strain $\gamma_k$ lies in a value ranging from 0.002 to 0.01;
the adiabatic shear deformation limit strain $\gamma_{\bar{c}}$ lies in a value ranging from 0.1 to 0.18;
the adiabatic shear deformation limit strain rate $\dot{\gamma}_{\bar{c}}$ lies in a value of $10^4$/sec;
the breakdown-point true shear strain $\gamma_z$ lies in a value ranging from 0.02 to 1.5; and
the impact occurrence strain rate $\dot{\gamma}_I$ lies in a value ranging from 50 to $10^2$/sec.

9. The computer-implemented method according to claim 6, wherein a fatigue life of the damage pattern 1 is subjected to a life prediction conducted based on a Miner's principle or corrected Miner's principle using an S-N diagram of the shear strain and a material and a Weibull establishment distribution.

10. An apparatus for determining patterns of damage being caused in a rolling contact element using a computer, the apparatus comprising:
inputting means for inputting input values including dimensional data, material characteristics, and loading condition material of the rolling contact element;

providing means for providing discrimination values of the rolling contact element;

calculating means for calculating a strain being caused and a strain rate being caused based on the input values to obtain a calculation result;

comparing means for comparing the calculation result to the discrimination values so as to judge the damage patterns; and outputting means for outputting information indicating the judged damage patterns using a display, wherein the discrimination values include five values related to a yield point shear strain, an adiabatic shear deformation limit strain, an adiabatic shear deformation limit strain rate, a breakdown-point shear strain, and an impact occurrence strain rate of the loading condition for making judgment on the damage patterns.

11. The apparatus according to claim 10, wherein the damage patterns are categorized as:

a pattern 1 representing a flaking caused by a rolling fatigue life;

a pattern 2 representing a brinelling in a sinking-up configuration followed by the damage;

a pattern 3 representing a brinelling in a sinking-in configuration followed by the damage;

a pattern 4 representing a flaking caused by an adiabatic shear deformation band; and a pattern 5 representing a crack or a chip.

12. The apparatus according to claim 11, wherein the damage patterns fall in:

the pattern 1 when Equation 1 is satisfied the pattern 2 when Equation 2 is satisfied the pattern 3 when Equation 3 is satisfied the pattern 4 when Equation 4 is satisfied the pattern 5 when Equation 5 is satisfied $$\gamma < \gamma_k \tag{Eq. 1}$$

$$\gamma_k \leq \gamma < \gamma_z \text{ and } \dot{\gamma} < \dot{\gamma}_I \tag{Eq. 2}$$

$$\gamma_k \leq \gamma < \gamma_z \text{ and } \dot{\gamma}_I \leq \dot{\gamma} \tag{Eq. 3}$$

$$\gamma_{\bar{c}} \leq \gamma < \gamma_z \text{ and } \dot{\gamma}_{\bar{c}} \leq \dot{\gamma} \tag{Eq. 4}$$

$$\gamma_z < \gamma \tag{Eq. 5}$$

where:
- $\gamma$ is the shear strain,
- $\dot{\gamma}$ is the shear strain rate,
- $\gamma_k$ is the yield point shear strain,
- $\gamma_{\bar{c}}$ is the adiabatic shear deformation limit strain,
- $\dot{\gamma}_{\bar{c}}$ is the adiabatic shear deformation limit strain rate,
- $\gamma_z$ is the breakdown-point true shear strain, and
- $\dot{\gamma}_I$ is the impact occurrence strain rate.

13. The apparatus according to claim 12, wherein:

the yield point shear strain $\gamma_k$ lies in a value ranging from 0.002 to 0.01;

the adiabatic shear deformation limit strain $\gamma_{\bar{c}}$ lies in a value ranging from 0.1 to 0.18;

the adiabatic shear deformation limit strain rate $\dot{\gamma}_{\bar{c}}$ lies in a value of $10^4$/sec;

the breakdown-point true shear strain $\gamma_z$ lies in a value ranging from 0.02 to 1.5; and the impact occurrence strain rate $\dot{\gamma}_I$ lies in a value ranging from 50 to $10^2$/sec.

14. The apparatus according to claim 10, wherein the rolling contact element is a ball bearing.

\* \* \* \* \*

UNITED STATES PATENT AND TRADEMARK OFFICE
CERTIFICATE OF CORRECTION

PATENT NO. : 7,577,555 B2  Page 1 of 1
APPLICATION NO. : 11/492775
DATED : August 18, 2009
INVENTOR(S) : Umeda et al.

It is certified that error appears in the above-identified patent and that said Letters Patent is hereby corrected as shown below:

Col 25 line 6 and Col 27 line 21 "sinking-up" should be corrected to "piling-up"

Signed and Sealed this

Seventeenth Day of November, 2009

David J. Kappos
*Director of the United States Patent and Trademark Office*